(12) United States Patent
Dai et al.

(10) Patent No.: US 10,526,438 B2
(45) Date of Patent: Jan. 7, 2020

(54) MULTI-FUNCTIONAL CARBAMATE HAVING SOFT-SEGMENTS, POLYISOCYANATE OBTAINED VIA SUBSEQUENT NON-PHOSGENE SYNTHESIS METHODS, URETHANE PREPOLYMER AND ELASTOMERIC URETHANE HAVING SOFT-SEGMENTS DERIVED THEREFROM, AND PREPARATION METHOD THEREOF

(71) Applicant: Great Eastern Resins Industrial Co., Ltd., Taichung (TW)

(72) Inventors: Shenghong A. Dai, Taichung (TW); Ching Hsuan Lin, Taichung (TW); Wei Ming Nien, Taichung (TW); Wen Chen Pan, Taichung (TW); Kevin Liao, Taichung (TW)

(73) Assignee: Great Eastern Resins Industrial Co., Ltd., Taichung (TW)

( * ) Notice: Subject to any disclaimer, the term of this patent is extended or adjusted under 35 U.S.C. 154(b) by 118 days.

(21) Appl. No.: 15/653,754

(22) Filed: Jul. 19, 2017

(65) Prior Publication Data

US 2018/0186918 A1 Jul. 5, 2018

(30) Foreign Application Priority Data

Dec. 29, 2016 (TW) .............................. 105143961 A

(51) Int. Cl.
| | | |
|---|---|---|
| *C08G 18/38* | (2006.01) | |
| *C07C 269/04* | (2006.01) | |
| *C08G 18/12* | (2006.01) | |
| *C07F 7/00* | (2006.01) | |
| *C07F 7/18* | (2006.01) | |
| *C08G 18/77* | (2006.01) | |
| *C08G 18/24* | (2006.01) | |
| *C08G 71/04* | (2006.01) | |

(52) U.S. Cl.
CPC ........ *C08G 18/3831* (2013.01); *C07C 269/04* (2013.01); *C07F 7/00* (2013.01); *C07F 7/1804* (2013.01); *C08G 18/12* (2013.01); *C08G 18/244* (2013.01); *C08G 18/778* (2013.01); *C08G 71/04* (2013.01); *Y02P 20/582* (2015.11)

(58) Field of Classification Search
None
See application file for complete search history.

(56) References Cited

U.S. PATENT DOCUMENTS

| | | | |
|---|---|---|---|
| 3,895,054 A | 7/1975 | Zajacek et al. | |
| 4,547,322 A | 10/1985 | Fukuoka et al. | |
| 5,360,931 A | 11/1994 | Bohmholdt et al. | |
| 7,402,689 B2 * | 7/2008 | Seelye | C07C 269/02 556/420 |
| 8,277,791 B2 | 10/2012 | Zheng et al. | |
| 2011/0054211 A1 | 3/2011 | Shinohata et al. | |
| 2013/0079542 A1 * | 3/2013 | Dai | C07C 269/04 560/25 |
| 2017/0015621 A1 | 1/2017 | Dai et al. | |

FOREIGN PATENT DOCUMENTS

| | | |
|---|---|---|
| CN | 102026964 A | 4/2011 |
| JP | 200148855 A | 2/2001 |
| KR | 960007802 B1 | 6/1996 |
| TW | 201417836 A | 5/2014 |
| TW | I443080 B | 7/2014 |
| TW | I561504 B | 12/2016 |
| TW | 201704202 A | 2/2017 |

OTHER PUBLICATIONS

Chen, H.-Y., et al., "Synthesis and trans-ureation of N,N'-diphenyl1-4, 4'-methylenediphenylene biscarbamate with diamines: a non-isocyanate route (NIR) to polyureas", J. Polymer Res., 2012, vol. 19, pp. 1-11.

Speckhard, T.A. et al., "Ultimate Tensile Properties of Segmented Polyurethane Elastomers: Factors Leading to Reduced Properties for Polyurethanes Based on Nonpolar Soft Segments", Rubber chemistry and technology, 1986, vol. 59, No. 3, pp. 405-429.

Tang, D., et al., "Well-defined Biobased Segmented Polyureas Synthesis via a TBD-catalyzed Isocyanate-free Route", Macromol. Rapid Commun., 2011, vol. 32, pp. 1379-1385.

Yamazaki, N., "The Reaction of Diphenyl Carbonate with Amines and Its Application to Polymer Synthesis", Journal of Polymer Science, 1979, vol. 17, pp. 835-841.

Taiwanese Office Action dated Dec. 13, 2017 for Taiwan Patent Application 1061213.

Taiwanese Search Report for Taiwan Application No. 106115527 dated Dec. 29, 2016 and English translation.

* cited by examiner

*Primary Examiner* — Christopher M Rodd
(74) *Attorney, Agent, or Firm* — Drinker Biddle & Reath LLP

(57) ABSTRACT

Method for producing flexographic printing plates from a photopolymerizable flexographic printing plate with a dimensionally stable support, photopolymerizable, relief-forming layer(s), and a digitally imagable layer. The method comprises (a) producing a mask by imaging the digitally imagable layer, (b) exposing the flexographic printing plate with a plurality of UV-LEDs on a UV-LED strip through the mask with actinic light, and photopolymerizing the image regions of the layer, and (c) developing the photopolymerized layer. In the UV-LED strip or in a separate strip, at least one ultrasonic sensor is arranged for determining the thickness of the flexographic printing plate for exposure. Depending on the measured thickness of the flexographic printing plate, the exposing of the flexographic printing plate is controlled in respect of: (i) number of exposure steps, exposure intensity, energy input per exposure step, duration of the individual exposure steps, and/or overall duration of exposure.

10 Claims, 6 Drawing Sheets

MULTI-FUNCTIONAL CARBAMATE HAVING SOFT-SEGMENTS, POLYISOCYANATE OBTAINED VIA SUBSEQUENT NON-PHOSGENE SYNTHESIS METHODS, URETHANE PREPOLYMER AND ELASTOMERIC URETHANE HAVING SOFT-SEGMENTS DERIVED THEREFROM, AND PREPARATION METHOD THEREOF

CROSS-REFERENCE TO RELATED APPLICATIONS

This application claims priority to Taiwanese Application No. 105143961, filed Dec. 29, 2016, which is incorporated herein by reference in its entirety.

BACKGROUND OF THE INVENTION

1. Field of the Invention

The present invention relates to a multi-functional carbamate having a soft segment (particularly siloxanyl) in its backbone, a polyisocyanate, a urethane prepolymer, and an elastomeric urethane. The present invention also provides a non-phosgene synthesis method for preparing the above-mentioned substances.

2. Description of the Related Art

Polyurethanes (PUs) are widely used in daily life. Polyurethanes are a class of polymers which contain carbamate functional units in their backbones and are generally prepared by reacting a polyisocyanate with a polyol or mixed polyols. As shown below, a diisocyanate is reacted with diols containing segments of different properties to produce a polyurethane:

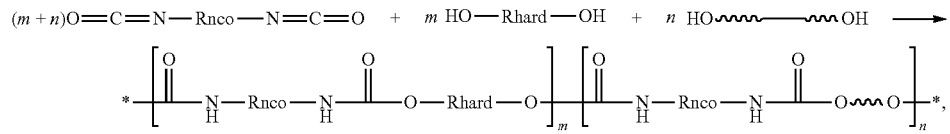

Polyurethanes are resistant to corrosion from a variety of acids, bases and organic solvents and are therefore often used as an alternative to rubber products in harsh environments. In general, the polyurethane may have a structure comprising a soft segment and a hard segment, where the hard segment is mainly formed by reacting a polyisocyanate group with a short-chain diol or diamine. By controlling the ratio of the rigid hard segment to the soft and flexible long-chain soft segment in the polyurethane, polyurethane materials with various mechanical functions can be obtained. Therefore, the polyurethane products have wear resistance, high-temperature tolerance, good sealing, sound insulation, good processability, good degradability, and other excellent characteristics, and are widely used in adhesives, coatings, low-speed tires, washers, car mats and other industrial areas, as well as in elastic materials for anti-vibration and anti-friction, for example, in soles, tractor and tank track pads, and athletic running tracks, and alternatives to natural rubber such as medical equipment and materials, condoms and so on.

At present, in the industrial production of isocyanates, the phosgenation method is still the main process, due to the advantages of simplicity, speed, high yield and low cost. However, the phosgene method has unavoidable shortcomings. First, the phosgene itself is highly toxic, and fatal even in trace amounts. Moreover, a large amount of hydrogen chloride gas is produced as a by-product during the phosgene process, which causes damage to the production equipment. With the rise of environmental protection awareness and the promotion of green chemistry, non-phosgene processes for production of isocyanates are being actively studied.

Isocyanates

Isocyanates refer to molecules bearing a —NCO group, which can be roughly classified as two types: aromatic isocyanates having a —NCO group directly attached to an aromatic group, such as methylenediphenyl diisocyanate (MDI) or toluene diisocyanate (TDI); and aliphatic or aromatic-aliphatic isocyanates having a —NCO group directly attached to a short-chain alkyl or alicyclic group, such as hexamethylene diisocyanate (HDI), isophorone diisocyanate (IPDI) or p-xylylene diisocyanate (XDI). The molecular structure of and the NCO content in the isocyanates play an important role in determination of their physical and chemical properties, for example, viscosity, crystallinity, thermal stability, and other functions and properties.

Polyols

Organic molecules having two hydroxyl functionalities are referred to as diols, while organic molecules having three hydroxyl functionalities are referred to as triols, and so on. The molecular chain structure, molecular weight and hydroxyl content of polyols play an important role in determination of their physical and chemical properties, such as viscosity, reactivity, and the like. It is known to those skilled in the art that the molecular weight of the polyol affects the physical state and mechanical [physical] properties of the polyurethane synthesized. Selection of a raw material suitable for the synthesis of polyurethane can be made on this basis.

Non-Phosgene Production of Isocyanates

With the rise of environmental protection awareness, attempts have been made since the 1970s by many scientists to develop non-phosgene processes for synthesizing isocyanates. Aliphatic or aromatic carbamates were synthesized by the ARCO Company (U.S. Pat. No. 3,895,054 A) in 1975, the Asahi Company (U.S. Pat. No. 4,547,322 A) in 1985, the BASF Company (U.S. Pat. No. 5,360,931 A) in 1986 and the Olin Company (KR 960007802 B1) in 1992 using a metal catalyst such as platinum, rhodium, lead and others, and then thermally cracking the carbamates to prepare aliphatic or aromatic isocyanates. However, these methods failed to gain wide practice in large-scale industrial production due to potential residues of the metal catalyst, high cost, relatively high thermal cracking temperature (250 to 410° C.), and poor yield and selectivity (50 to 80%).

Moreover, if the ester group structure of the polyurethane contains a less optimal leaving group (for example, alkyl, such as methyl, ethyl, and butyl), a large amount of energy is consumed—that is, a relatively high temperature is required—during the process for forming an isocyanate by removing the alkyl from the structure via thermal cracking (where by-product alkyl alcohol is produced). Furthermore, the isocyanate is susceptible to a reversible reaction with the by-product alcohol, whereby the yield is reduced. To solve such problems, N. Yamazaki et al. (*The reaction of diphenyl carbonate with amines and its application to polymer synthesis*. Journal of Polymer Science Part A: Polymer Chemistry, 1979. 17(3): p. 835-841) disclosed, in 1979, a method for synthesizing a biscarbamate through the reaction of a diphenyl carbonate with a diamine compound using 2-hydroxypyridine as a catalyst, where the carbamate has a terminal phenyl group, instead of the previously used methyl or ethyl. The disadvantage includes using an expensive catalyst. In addition, when an aromatic diamine is used as a raw material, selectivity for and yield of the product only up to 80% as well as slow reaction rate could be achieved. If the reaction temperature is elevated for increasing the reaction rate, the yield of the by-product urea increases accordingly.

In the method published by LIN Zhaoxing et al. (in R.O.C. Taiwan Patent No. 1443080), 4,4'-methylene diphenylamine (4,4'-MDA) is reacted with diphenyl carbonate (DPC) in the presence of benzoic acid as a catalyst in toluene (solvent) and diphenyl 4,4'-methylene diphenylcarbamate (4,4'-DP-MDC) is successfully prepared.

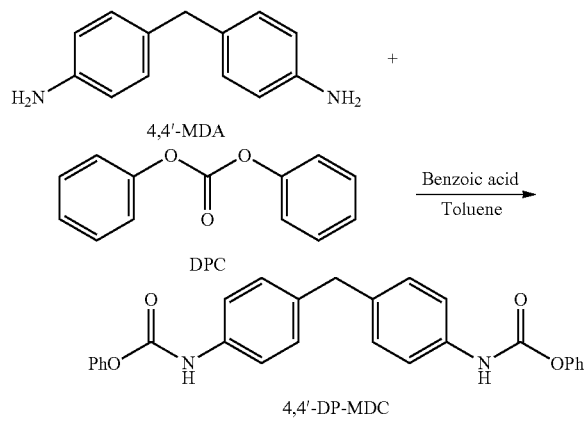

In 2011, Asahi Company proposed a process similar to the non-phosgene method mentioned above:

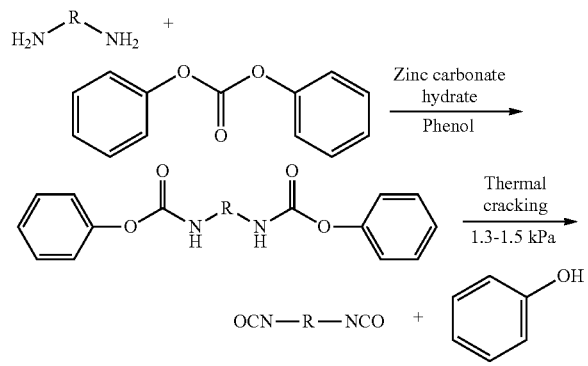

and then an isocyanate is further prepared through a continuous process. In this process, a diamine compound and diphenyl carbonate are also used as reaction materials, and a metal hydrate catalyst (zinc carbonate dihydrate) and phenol as solvent are added. The reaction takes place at 50° C. to produce biscarbamates, which are then thermally cracked in a distillation column to obtain a high-purity, high-yield isocyanate. The reactant diphenyl carbonate can be successfully retrieved and the phenol recovered. However, the time required by the whole process is as long as 10 days.

In 2012, 4,4'-MDI was successfully prepared by CHEN Xueyong et al. through a non-phosgene two-step process (*Non-phosgene Route to* 4,4'-*Methylenediphenylene Diisocyanate*. 2012.). In the first carbonylation step, optimization is performed with respect to the choice of the catalyst carboxylic acid, the amount of the catalyst, the amount of the reactants and the recovery and reuse of the reactants and catalyst to obtain preferred reaction conditions Meanwhile, the mechanism of reaction of the carbonylation catalyzed by benzoic acid is revealed, and it is envisaged to add a tertiary amine as a co-catalyst, whereby the reaction temperature of 80° C. is successfully lowered to 45° C., and the yield is up to 99%. In the second thermal cracking step, unlike the prior art, where a temperature as high as to 250° C., reduced pressure and other conditions are generally required, 4,4'-MDI is successfully produced by reacting for 2.5 hrs. at 210° C. in a non-polar solvent n-dodecane without using any metal catalyst, and 4,4'-MDI can be resolved by distillation or crystallization, where the yield is 75-80%, and the recovery rate of both the by-product phenol and the solvent n-dodecane is up to 95%. By means of the non-phosgene two-step process, the use of phosgene is avoided, recoverable chemical products are produced, which can be separated under mild conditions, and high-yield high-purity 4,4'-MDI is prepared. The produced 4,4'-MDI can be subsequently used in the preparation of raw materials for synthesizing polyurethane and polyurea polymers.

In 2015, an aliphatic diisocyanate was successfully prepared by LIN Weixing et al. (in R.O.C. Taiwan Patent Application No. 104123293) with decamethylenediamine (DMDA), hexamethylenediamine (HMDA), butylmethylenediamine (BMDA) and other aliphatic diamines through a one-pot process. In this process, diphenyl ether (DPE) is used as a solvent, an aliphatic diamine is reacted with diphenyl carbonate to form a biscarbamate, which is cracked by directly heating it to obtain an aliphatic diisocyanate. During this two-step one-pot process, no toxic phosgene or metal catalyst is used, and the operation time is short, which conforms to the trend of green chemistry. Therefore, the process is expected to be practical for industrialization.

In summary, due to the use and the production of too many corrosive substances in the phosgene process, as indicated by the fact that the phosgene itself is highly toxic and produces a highly corrosive and dangerous by-product of hydrogen chloride gas, the phosgene process of preparing isocyanates will inevitably be replaced in the future. Therefore, avoiding the use of phosgene and halides in the process is one of the key goals in promoting green chemistry in recent years. However, the aforesaid non-phosgene process partially involves a non-green catalyst or a non-green organic solvent; if it is possible to eliminate the use of said catalyst and organic solvent, it will be a great advancement for the promotion of green chemical processes in production of isocyanates.

Non-Phosgene Production of Polyurethane

In 1979, N. Yamazaki et al. disclosed a method for synthesizing a polyurethane (*Ultimate tensile properties of segmented polyurethane elastomers: factors leading to reduced properties for polyurethanes based on nonpolar soft segments*. Rubber chemistry and technology, 1986. 59(3): p. 405-431.), in which diphenyl carbonate (DPC) is transesterified with MDA in 2-hydroxypyridine to prepare diphenyl 4,4'-methylene diphenylcarbamate (4,4'-DP-MDC) with a yield of 68%, which is then transesterified with a diol in the presence of a catalyst magnesium chloride to prepare a polyurethane polymer.

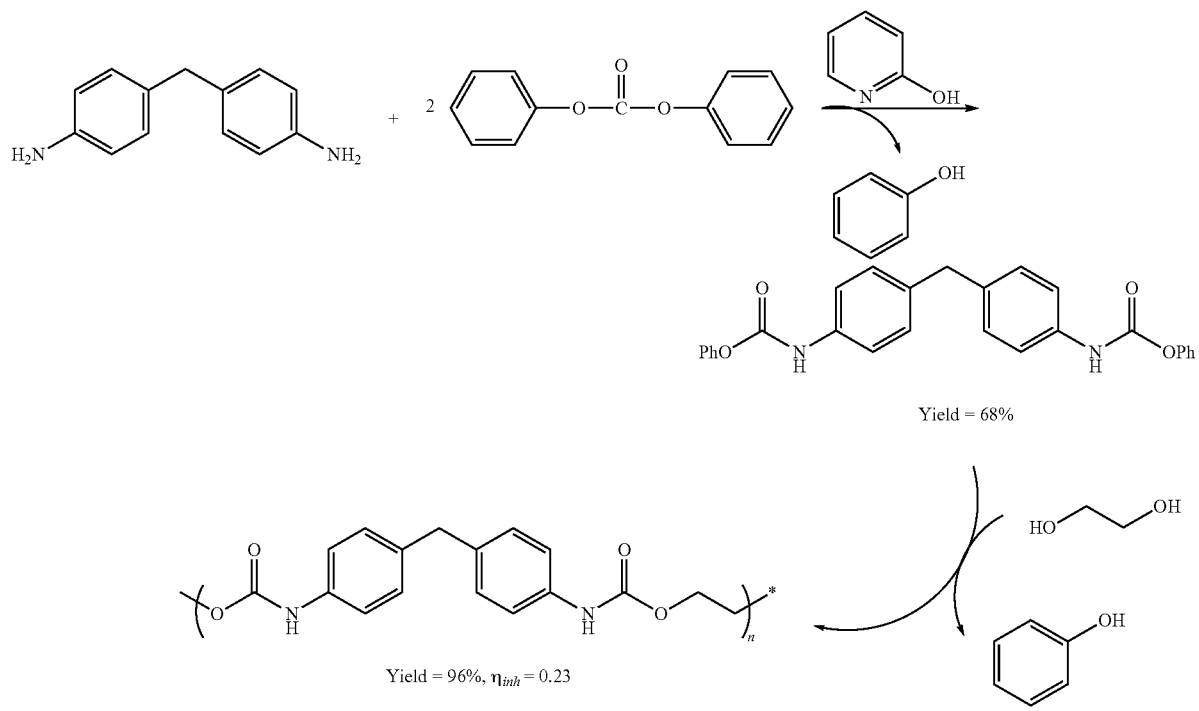

Although the yield of the product thus obtained is up to 96%, the molecular weight of the synthesized polyurethanes is insufficient ($\eta_{inh}$=0.23) because only a rigid chain polyurethane was prepared but no polyol is used during preparation thereof, resulting in undesirable elastomeric mechanical and thermal properties. Also in the literature, another study of N. Yamazaki et al. involves the preparation of a polyurea polymer with diphenyl carbonate and MDA in pyridine in the presence of magnesium chloride, where the yield is 80%. However, in the study of N. Yamazaki et al, although the use of an isocyanate is avoided so that there is no need to use the phosgene method for preparing the polymer, the process still involves the use of a halogen-containing catalyst, and is thus not a process that completely conforms to the requirements of green chemistry. Furthermore, the molecular weight of the polymer formed is still low.

In the study of C. E. Koning et al. in 2011, a raw material and catalyst of natural sources are used.

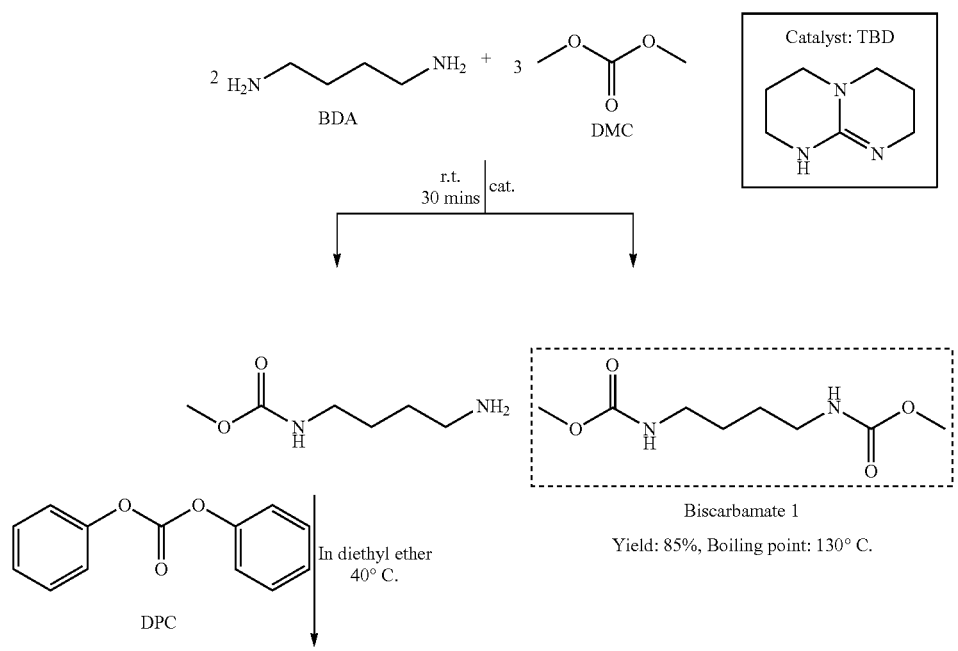

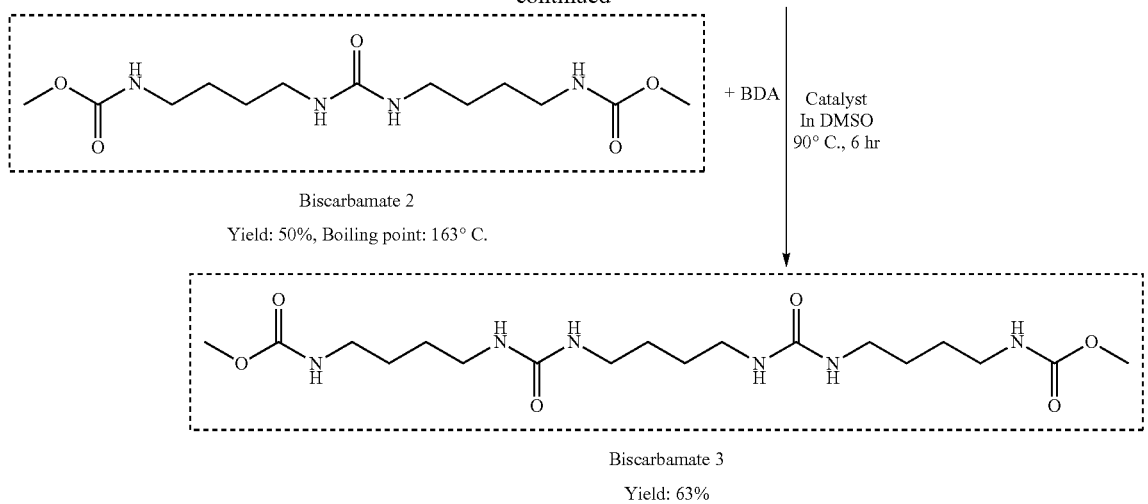

Biscarbamate 2
Yield: 50%, Boiling point: 163° C.

Biscarbamate 3
Yield: 63%

Biscarbamates of different chain lengths are initially synthesized and used as intermediates. Then, the rigid biscarbamates of three different chain lengths are used as a raw material, diethylene glycol diethyl ether (EGDEE), dimethyl acetamide (DMAc) or N-methylpyrrolidone (NMP) is used as a solvent, and PPGda-400 or PPGda-2000 (Poly(propylene glycol) bis(2-aminopropyl ether)) is used as a soft segment; and the reaction occurs at 130° C. for 4-24 hrs. for synthesizing polyurethanes (PUs) by melt-polymerization. During the polymerization, transesterification takes place, and a hard segment with a constant length is formed in respective PUs, where the length of the hard segment determines the property of PUs. In the literature, the metal catalyst previously used in the art is replaced by an organic catalyst, and a product 1,4-butanediamine (BDA) derived from a natural product is used as a starting material. However, 1,5,7-triazabicyclo[4.4.0]dec-5-ene (TBD) is used as a catalyst in the process so a synthesis method without catalyst cannot be achieved.

Introduction of a PDMS Soft Segment to a PU Polymer

In recent years, polydimethylsiloxane (PDMS) is often used as a soft segment that is introduced into the backbone of a PU polymer, which has proved able to effectively improve the characteristics of a traditional PU, such as softness, flexibility, thermal stability, heat resistance, moisture resistance, hydrophobicity and tolerance to solvents, acids and bases, etc. Because of the introduction of the non-polar PDMS material as a soft segment, the degree of phase separation of the product PU and tactile comfort of the material are greatly improved, compared with the traditional PU. For example, a polyurethane having a soft segment is applicable to fabric, fabric coating, biomedical contacting lens, anti-scale coating and other areas, to impart or modify a property as desired in the product.

Therefore, there is still a need for polyurethane molecules that has a special soft segment and exhibits good mechanical properties prepared by non-phosgene synthesis.

SUMMARY OF THE INVENTION

Therefore, the present invention provides a raw material for preparing a PU polymer having a soft segment and particularly siloxane as a main soft segment structure in its backbone, such as a biscarbamate, a polyisocyanate, and an elastomeric uethane prepolymer, a method for preparing the same, and use thereof in the synthesis of a specialty PU polymer. The present invention also provides a non-phosgene synthesis method for preparing the polyurethane substance having siloxane as a main soft segment structure as mentioned above.

The preparation of the aforesaid substance by non-phosgene synthesis in the present invention is based on the extended application of the Invention Patent Application R.O.C. Taiwan No. 104123293 (corresponding to US Publication No. 2017/0015621 A1), which is incorporated herein by reference in its entirety.

Each aspect and each embodiment of the invention disclosed herein is intended to be individually combined with all other disclosed aspects and embodiments of the present invention into all possible combinations thereof.

In the context of the specification and the claims, the singular forms "a", "an" and "the" include plural referents, unless specifically indicated otherwise. Unless otherwise stated, any and all examples or exemplary language (e.g., "such as") provided herein are merely used for better illustration of the present invention, instead of limiting the scope of the present invention. The language in this specification should not be construed as indicating that any element not claimed is necessary for the practice of the present invention.

It is to be understood that any numerical range recited in this specification is intended to include all sub-ranges and values encompassed therein. For example, a range from "50 to 70° C." includes all sub-ranges and specific values (e.g. from 58° C. to 67° C. and from 53° C. to 62° C., 60° C. or 68° C.) between the stated minimum value of 50° C. and the stated maximum value of 70° C., inclusive, that is, ranges from a minimum value that is greater than or equal to 50° C. to a maximum value that is equal to or less than 70° C. Since the numerical ranges disclosed are continuous, they contain each numerical value between the minimum and maximum value. Unless otherwise specified, the various numerical ranges indicated in this specification are approximate.

Definitions

The term "carbamate" as used herein refers to a molecule having a

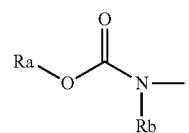

group, where $R_a$ is an organic group and $R_b$ is hydrogen or an organic group; the organic group can be, for example, a hydrocarbyl group.

The multi-functional carbamate as used herein refers to a molecule having two or more carbamate groups. For ease of expression, the terms "biscarbamate", "triscarbamate", and so on are used to particularly indicate the number of the carbamate group contained in the molecule.

The term "soft segment" as used herein refers to a (long-chain) structural unit that, when present in a polymer chain, can provide more flexibility to the polymer than a hydrocarbon segment. The common soft segment is derived from a long straight-chain compound having a polyether group, a polyester group or a siloxanyl group and generally has a molecular weight of 1000 to 3000. Examples include those having a polyether group, for example, polytetramethylene ether diol, polyethylene ether diol, and polypropylene ether diol; those having a polyester group, for example, polycarbonate diol and poly(butylene adipate) diol; and diols and diamines having a siloxanyl group, etc.

The term "siloxanyl" as used herein refers to a group that comprises a —Si(CH$_3$)$_2$—O—Si(CH$_3$)$_2$— unit, and is preferably in the form of

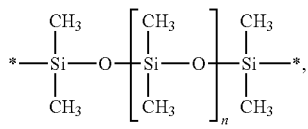

in which n is an integer of at least 0.

The term "hard segment" as used herein refers to a rigid segment of low degree of freedom present in a polymer chain, and generally refers to a moiety formed by addition of a short-chain diol (e.g. butanediol (BDO)) with a short-chain diisocyanate during the synthesis of polymer. The common hard segment includes a hydrocarbon segment, for example, a PU segment formed through reaction of a diol having a short-chain alkyl group (e.g. $C_{2-6}$ alkyl, such as hexyl, butyl, ethyl and the like) or a diamine having a short-chain alkyl group with an di-isocyanate having a short-chain alkyl, cycloalkyl or phenyl group (for example, MDI, TDI, HDI, PPDI, and IPDI).

The term "isocyanate" as used herein refers to a molecule bearing an —NCO functional group. The term "polyisocyanate" is intended to encompass a molecule bearing two or more isocyanate groups. For ease of expression, the terms "diisocyanate," "triisocyanate" and so on are used to particularly indicate the number of the isocyanate group contained in the molecule.

The term "polyurethane" as used herein refers to an oligomer or a polymer comprising multiple carbamate unit(s).

The term "hydrocarbyl" as used herein refers to an organic group having a main structure composed exclusively of carbon and hydrogen atoms, for example, alkyl, cycloalkyl, alkenyl, cycloalkenyl, alkynyl, aryl, and the like. The hydrocarbyl or a specific form thereof as used herein may be unsubstituted or optionally substituted with a suitable substituent, for example, halo, nitro, hydroxyl, cyano, alkyl, and so on.

The term "alkyl" as used herein refers to a linear or branched group derived from an alkane molecule and having a general formula of $C_nH_{2n+1}$. Examples of the alkyl group include, but are not limited to, methyl, ethyl, n-propyl, i-propyl, n-butyl, i-butyl, s-butyl, t-butyl, $C_5$ alkyl and isomeric forms thereof, $C_6$ alkyl and isomeric forms thereof, $C_7$ alkyl and isomeric forms thereof, and an alkyl group having eight or more carbon atoms and isomeric forms thereof.

The term "cycloalkyl" as used herein refers to a group derived from a fully saturated hydrocarbon molecule that has at least one ring in its structure. Examples of the cycloalkyl group include, but are not limited to, cyclopropyl, cyclobutyl, cyclopentyl, methylcyclobutyl, cyclohexyl, and other cycloalkyl groups having six or more carbon atoms and isomeric forms thereof.

The term "alkenyl" as used herein refers to a group derived from a molecule having one or more carbon-carbon single bonds in an alkane molecule replaced with a carbon-carbon double bond(s). Examples of the alkenyl group, include, but are not limited to, ethenyl, propen-1-yl, propen-2-yl, propen-3-yl, allenyl, and other alkenyl groups having four or more carbon atoms and an isomer thereof.

The term "cycloalkenyl" as used herein refers to a group derived from a hydrocarbon molecule having at least one ring and at least one carbon-carbon double bond in the ring structure. Examples of the cycloalkenyl group, include, but are not limited to, for example, cyclopropenyl, cyclobutenyl, and other cycloalkenyl groups having four or more carbon atoms and isomeric forms thereof.

The term "alkynyl" as used herein refers to a group derived from a molecule having one or more carbon-carbon single bonds in an alkane molecule replaced with a carbon-carbon triple bond(s). Examples of the alkenyl group, include, but are not limited to, for example, ethynyl, propynyl, butynyl and isomeric forms thereof, and other alkynyl groups having four or more carbon atoms and isomeric forms thereof.

The term "aryl" as used herein refers to a group derived from an aromatic hydrocarbon molecule. Examples of the aryl group include, but are not limited to, monocyclic aryls for example, phenyl; bicyclic aryls, for example, biphenylyl, and naphthyl; or polycyclic aryls, for example, anthryl, phenanthryl, and the like.

The term "-ylene" as used herein refers to a divalent hydrocarbon group attached to two structures/moieties. For example, "alkylene" denotes a divalent group derived from an alkane molecule. Examples of compounds having an alkylene group include 1,2-ethylene diol, hexamethylene diamine, hexamethylene diisocyanate and so on.

The term "amine" as used herein refers to a molecule having at least one —NR'R" group in the molecular structure, where R' and R" may be independently hydrogen or hydrocarbyl. The term "polyamine" refers to a molecule having two or more —NR'R" groups in the structure. For ease of expression, the phrases "diamine", "triamine", and so on are also used to particularly indicate the number of the —NR'R" group contained in the molecule.

The term "alcohol" as used herein refers to a molecule having at least one —OH group in the molecular structure. The term "polyol" refers to a molecule having two or more —OH groups in the structure. For ease of expression, the phrases "diol", "triol" and so on are also used to particularly indicate the number of the —OH group contained in the molecule.

In case of contradiction, the definitions of groups or molecules mentioned are given in accordance with the order of importance of the functional groups. The naming rules may also make reference to the nomenclature announced by the International Union of Pure and Applied Chemistry (IUPAC).

Multi-Functional Carbamate Having a Soft Segment

The raw materials for synthesizing polyurethane mainly include polyisocyanates and polyols. To produce a polyurethane having improved physical and/or chemical properties, to introduce additional mechanical property thereto and to customize the properties of a product, a soft segment (for example, siloxanyl) is introduced into the backbone of a polyurethane during synthesis. For the purpose of introducing a special functional structure such as siloxanyl, theoretically, a polyurethane having a siloxanyl group can be produced by using a polyisocyanate having a long-chain siloxanyl group or a polyol having a siloxanyl as a reactant. However, no commercial products for polyisocyanates having a siloxanyl group are currently available in the market, and a polyol having a siloxanyl group is difficult to mix and cannot successfully react with the component(s) for the reaction (comprising for example, an isocyanate prepolymer, a chain extender etc.) employed in a conventional PU synthesis method, mainly because of low reactivity and miscibility.

Therefore, an object of the present invention is to provide a multi-functional carbamate (for example, a biscarbamate) having a soft segment in its backbone, so as to avoid the problems above. The multi-functional carbamate having a soft segment in its backbone may be further thermally cracked into a polyisocyanate, which is highly reactive and miscible with a commonly used polyol and other reactants, thus facilitating the progress of the reaction.

The biscarbamate having a siloxanyl group as a soft segment in its backbone provided in the present invention may, for example, have a structure of general Formula (1) below:

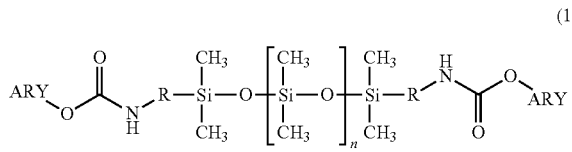

in which each R is independently a hydrocarbylene, each ARY is independently aryl, and n=2 to 30. For example, R may be a linear $C_{1-16}$ hydrocarbylene, such as methylene, dimethylene, trimethylene, tetramethylene, pentamethylene, hexamethylene, octamethylene or dodecamethylene; $C_{3-16}$ cyclohydrocarbylene, such as cyclopentylene, cyclohexylene cycloheptylene, cyclooctylene, bis(cyclohexyl), or alkyl-substituted cyclooctylene; alkyl-substituted cyclohydrocarbylene, such as methylcyclopentylene, ethylcyclopentylene, methylcyclohexylene, ethylcyclohexylene, propylcyclohexylene, butylcyclohexylene, pentylcyclohexylene or hexylcyclohexylene; $C_{3-16}$ cyclohydrocarbylene substituted with two identical or different $C_{1-6}$ alkyl groups, such as dimethylcyclohexylene, and diethylcyclohexylene; cyclohydrocarbylene substituted with three alkyl groups, such as 1,5,5-trimethylcyclohexylene, 1,5,5-triethylcyclohexylene, 1,5,5-tripropylcyclohexylene or 1,5,5-tributylcyclohexylene. ARY may be phenyl, methylphenyl, or ethylphenyl. Preferably, R is $C_{3-6}$ alkylene; ARY is phenyl; and preferably n=4-20.

The equivalent of the siloxane unit present in the biscarbamate having a siloxanyl group in its backbone may be adjusted as desired according to the properties of the final product to be achieved. For example, the siloxane unit may account for 30 to 80%, and preferably 50 to 65% of the total weight of the polymer.

Method for Preparing a Soft Segment Having Multi-Functional Carbamate Groups

The multi-functional carbamate provided in the present invention may be obtained by reacting a diamine having a soft segment (for example, siloxanyl (preferably long-chain siloxanyl), other groups capable of forming a soft segment (preferably a polyether group or a polyester group, or any combinations thereof) in its backbone with a diaryl carbonate at a suitable ratio, where a by-product aromatic phenol is recovered at the same time. In this method, neither catalyst nor relatively high reaction temperature are required to be used, and the yield of the product and the recovery rate of the by-product are both excellent. The reaction can even take place without additionally adding a solvent because the diamine having a soft segment is in liquid state at room temperature and is miscible with other reactants.

Diamine Having a Siloxanyl Group

The diamine having a siloxanyl group useful in the present invention is a liquid with good fluidity and low melting point, which may, for example, have a structure of general Formula (2):

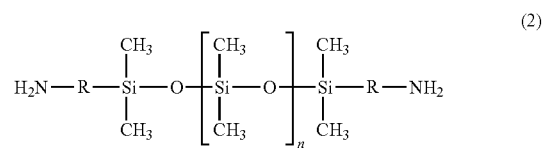

in which R and n are as defined above.

Particularly, the diamine compound having a siloxanyl group is preferably diaminopolydimethylsiloxane.

The molecular weight of the diamine having a siloxanyl group may be 200 to 3000 g/mol, and the viscosity at 25° C. may be 4 to 550 mm$^2$/s. In the diamine having a siloxanyl group, the proportion of the siloxanyl group can be obtained through calculation according to the molecular weight and the design of the molecular structure. For example, in a diamine of Formula (2) where R is —$C_3H_6$—, the siloxanyl group accounts for about 40.0 to 97.0% by weight of the molecule. Diamines having different proportions of siloxanyl groups are properly selected and used as a reactant as well as the amount of the reactant is determined, both according to the properties of subsequent products (for example, a biscarbamate, or a polyurethane) to be prepared and the proportion of the soft segment.

In such a preparation method, a polyamine having a siloxanyl group may also be used as a reactant in the preparation of a multi-functional carbamate.

Diaryl Carbonate

The diaryl carbonate used in the method of the present invention is a compound of Formula (3) below:

in which $R^1$ and $R^2$ represent an aromatic group having 6 to 30 carbon atoms, and preferably an aromatic group having 6 to 12 carbon atoms. Where the aryl has two or more substituents, these substituents may be identical or different.

The substituent on $R^1$ and $R^2$ is preferably selected from an alkyl or cycloalkyl group having 1 to 12 carbon atoms, for example, methyl, ethyl, propyl, and butyl; an aralkyl group having 7 to 15 carbon atoms, for example, phenylmethyl and phenylethyl; an aryl group having 6 to 14 carbon atoms, for example, phenyl and methylphenyl; an unsubstituted or substituted alkoxy group having 1 to 12 carbon atoms, for example, methoxy, ethoxy, propoxy, butoxy, and trifluoromethoxy; a thioalkoxy group having 1 to 12 carbon atoms, for example, thiomethoxy, and thioethoxy; an aryloxy group having 6 to 14 carbon atoms, for example, phenoxy; halo, for example, fluoro, chloro, and bromo; nitro; hydroxy; cyano; and dialkylamino, for example, dimethylamino.

Substituted and unsubstituted $R^1$ and $R^2$ include, for example, but are not limited to, phenyl, naphthyl, anthryl, phenanthryl, methylphenyl, dimethylphenyl, ethylphenyl, propylphenyl, octylphenyl, nonylphenyl, dodecylphenyl, biphenyl, methoxyphenyl, chlorophenyl, dichlorophenyl, trichlorophenyl, pentachlorophenyl, bromophenyl, dibromophenyl, tribromophenyl, pentabromophenyl, nitrophenyl, dinitrophenyl, hydroxyphenyl, cyanophenyl, and dimethylaminophenyl.

In addition, such aryl groups include ortho-, meta-, and para-isomers, and the substituents attached to the aryl group include n-, iso-, sec- and tert-isomers.

Preferably, diphenyl carbonate, bis(2-methylphenyl) carbonate, bis(4-chlorophenyl) carbonate, bis(4-nitrophenyl) carbonate, and bis(3,5-dimethoxyphenyl) carbonate are used, and more preferably, diphenyl carbonate is used.

Preparation Procedure

First, a diaryl carbonate is added to a suitable reactor and heated until it becomes a liquid. A polyamine having a soft segment in its backbone is then added to the reactor, and the reaction occurs upon mixing and stirring at a suitable reaction temperature. The molar ratio of the polyamine to the diaryl carbonate may range from 1:2 to 1:6, preferably from about 1:2 to 1:4, and most preferably from about 1:2.00 to 1:2.15. The reaction temperature may be, for example, 60 to 100° C., and preferably 80 to 100° C.

The progress of the reaction can be determined by IR spectroscopy by detecting the change of the intensity of the carbonate peak (for example, at 1780 $cm^{-1}$) and of the carbamate peak (for example, at 1717 $cm^{-1}$) in the reactants. Upon completion of the reaction, the crude product thus prepared is directly used in a subsequent reaction to prepare a polyisocyanate having a soft siloxane segment, and the subsequent reaction is preferably conducted in a dry and low-moisture atmosphere of pure nitrogen or an inert gas, for example, pure helium.

Polyisocyanate Having a Soft Segment (or a Soft Segment with Polyisocyanate End-Group)

The present invention also provides a polyisocyanate having a soft segment in its backbone, which is used as a material in the preparation of a polyurethane prepolymer and polymer having a soft segment in their backbone.

The polyisocyanate having a soft segment in its backbone according to the present invention may, for example, have a structure of general Formula (4) below:

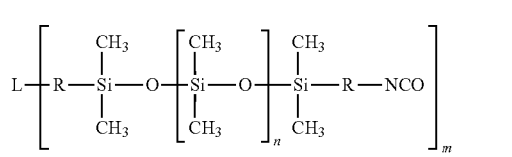

(4)

in which R and n are as defined above, L is a linking group (for example, that formed by reaction with NCO) or a direct bond, and m is an integer of at least 2; n in each unit may be identical or different; and L is, for example, an allophanate group or an isocyanurate group (trimer group).

Alternatively, the diisocyanate having a soft segment in its backbone according to the present invention may have a structure of general Formula (5) below:

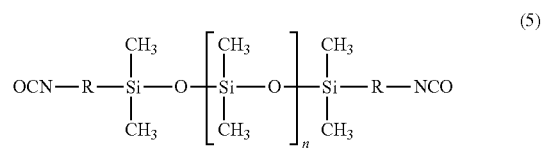

(5)

in which R and n are as defined above.

Method for Preparing a Polyisocyanate Having a Soft Segment

Two-Step Method

The polyisocyanate having a soft segment in its backbone according to the present invention may be prepared through a two-step method comprising the steps of: (1) reacting a polyamine having a soft segment (for example, siloxanyl) in its backbone with a diaryl carbonate at a suitable ratio to obtain a multi-functional carbamate (preferably a biscarbamate) having a soft segment; and then (2) thermally cracking the multi-functional carbamate (preferably a biscarbamate) having a soft segment in its backbone. The product thus obtained also comprises a reaction product of a diisocyanate with the biscarbamate formed during the thermal cracking of the multi-functional carbamate.

Step (1) has been described in detail above. In step (2), the multi-functional carbamate (preferably a biscarbamate) having a soft segment in its backbone according to the present invention is transferred to a suitable reactor, and then thermally cracked preferably under a reduced pressure, where a by-product aromatic phenol is recovered at the same time. During the reaction process, the progress of the reaction can be determined by IR spectroscopy by detecting the change of the intensity of the carbamate peak (for example, at 1717 $cm^{-1}$) and of the isocyanate peak (for example, at 2270 $cm^{-1}$) of the reaction solution. Upon completion of the reaction, the product containing the isocyanate or polyisocyanate is collected for use in the subsequent synthesis of a polyurethane.

The reaction temperature may be from 100 to 250° C., preferably from 160 to 220° C. The reduced reaction pressure may be 100 to 0.01 mmHg; preferably 50 to 0.1 mmHg.

One-Pot Method

The polyisocyanate having a soft segment in its backbone according to the present invention may also be synthesized through a one-pot method comprising a one-pot reaction in which steps (1) and (2) in the two-step method are carried out in combination. The method comprises: reacting a polyamine having a soft segment (for example, siloxanyl) with a diaryl carbonate at a suitable ratio, and then performing the subsequent thermal cracking step in the same reactor, to prepare a polyisocyanate having a soft segment in its backbone. The reaction conditions in the one-pot method are substantially the same as those in the two-step method. However, the reaction time, reaction apparatus cost and energy cost can be reduced; for example, the reaction can be completed without introducing an additional solvent.

Polyurethane Having a Soft Segment

An object of the present invention is to provide a polyurethane having a soft segment (for example, siloxanyl) in its backbone, in which the polyurethane has improved physical and/or chemical properties, and retains or provides special mechanical and excellent physical properties.

Compared with common polyurethanes, the polyurethane having a soft segment provides good chemical resistance (for example, acid and base resistance), high hydrophobicity, and low surface tension. A final product manufactured therefrom is pleasing to the touch, has a wide range of anti-freeze temperature (low Tg), and provides mechanical properties comparable to those of a common polyurethane.

The polyurethane having a soft segment provided in the present invention preferably has at least one of the following characteristics: a contact angle of at least 900 and preferably at least 1000; and a glass transition temperature ranging from −75 to 25° C., and preferably from −55 to 20° C. as measured by Differential Scanning Calorimetry (DSC).

Method for Preparing a Polyurethane Having a Soft Segment

The polyurethane having a siloxanyl group provided in the present invention can be obtained by reacting an isocyanate having a soft segment in its backbone, polyol and an optional chain extender (for example, an isocyanate chain extender as a hard segment). The ratio of the soft segment to the hard segment in the polyurethane may be adjusted based on the demand; for example, the hard segment may be in the range of 20 to 70%, and preferably 35 to 60% by weight Relative to the moles of the isocyanate having a siloxanyl group that are taken as reference (that is, 1 eq.), the polyol is used at 3 to 10 molar equivalents; and the chain extender is used at 2 to 9 molar equivalents.

Polyol

The polyol of the present invention may, for example, have a structure of general Formula (6) below:

$$(HO)_p\text{—}R^3 \qquad (6)$$

in which $R^3$ is a p-valent group derived from a linear or branched $C_{1-16}$ hydrocarbyl or a $C_{3-16}$ cyclohydrocarbyl, where p is an integer of at least 2.

Examples of the polyol may include, for example, ethylene glycol, propylene glycol, butylene glycol, pentanediol, hexanediol, glycerol, and so on.

Chain Extender

The chain extender in the present invention refers to a compound for extending the chain length of the hard segment in the polymer which bears a suitable functional group (for example, an alcohol group, an amino group and an isocyanate group) at both ends, including a prepolymer synthesized therefrom. The chain extender can also be used to control the ratio of the soft segment to the hard segment in the polymer chain. Examples of the chain extender include an isocyanate containing no soft segment, for example, 1,6-hexamethylene diisocyanate (HDI), 4,4-methylenediphenyl diisocyanate (MDI), toluene diisocyanate (TDI), 1,4-phenylene diisocyanate (PPDI), isophorone diisocyanate (IPDI), dicyclohexyl methane diisocyanate ($H_{12}$MDI), m-tetramethylxylene diisocyanate (TMXDI), and p-xylylene diisocyanate (XDI), etc.

Direct PU Synthesis Method

In one aspect, the method for preparing a polyurethane having a soft segment according to the present invention comprises a step of reacting a polyisocyanate having a soft segment (for example, siloxanyl) in its backbone, a polyol and an optional chain extender under suitable reaction conditions. This synthesis method is similar to a conventional synthesis method for polyurethanes, except that polyurethanes having various soft to hard segment ratios and desired properties can be obtained by adjusting the proportion of each component.

In another aspect, the method for preparing a polyurethane having a soft segment according to the present invention is a one-pot method comprising the following steps carried out in the same reactor: reacting a polyamine having a soft segment with a diaryl carbonate to produce a multifunctional carbamate (preferably a biscarbamate) having a soft segment; thermally cracking the multi-functional carbamate, to produce a polyisocyanate having a soft segment; and further adding a polyol and an optional chain extender and reacting them under suitable reaction conditions to produce a polyurethane having a soft segment.

Method for Synthesis Via a Prepolymer

Another method for preparing a polyurethane having a soft segment according to the present invention comprises a step of preparing a urethane prepolymer having a soft segment. A polyisocyanate having a soft segment is initially mixed with an excessive amount of a polyol, and then reacted under suitable reaction conditions to produce a prepolymer having a soft segment which has a terminal carbamate group bearing a hydroxyl group derived from the polyol; and then the prepolymer (and the unreacted polyol) is mixed with a chain extender, and reacted under suitable reaction conditions to produce a polyurethane. The progress of the reaction may be detected by IR spectroscopy during the synthesis of the prepolymer. Moreover, compared with a common reactant (for example, polyol) having a soft segment (particularly, having a high proportion of siloxanyl groups), the urethane prepolymer having a soft segment of the present invention is more highly compatible with other isocyanates, and thus various polyurethanes having a siloxanyl soft segment can be more easily synthesized therefrom.

The prepolymer having a terminal carbamate group bearing a hydroxyl group may, for example, have a structure of Formula (7) below:

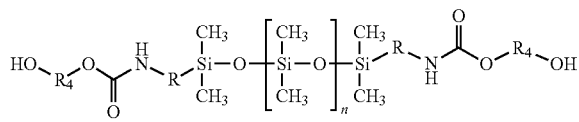

in which R and n are as defined above, and $R^4$ is as defined for R above.

BRIEF DESCRIPTION OF THE DRAWINGS

The invention will be described according to the appended drawings, in which.

PREFERRED EMBODIMENTS OF THE PRESENT INVENTION

Figure 1A:
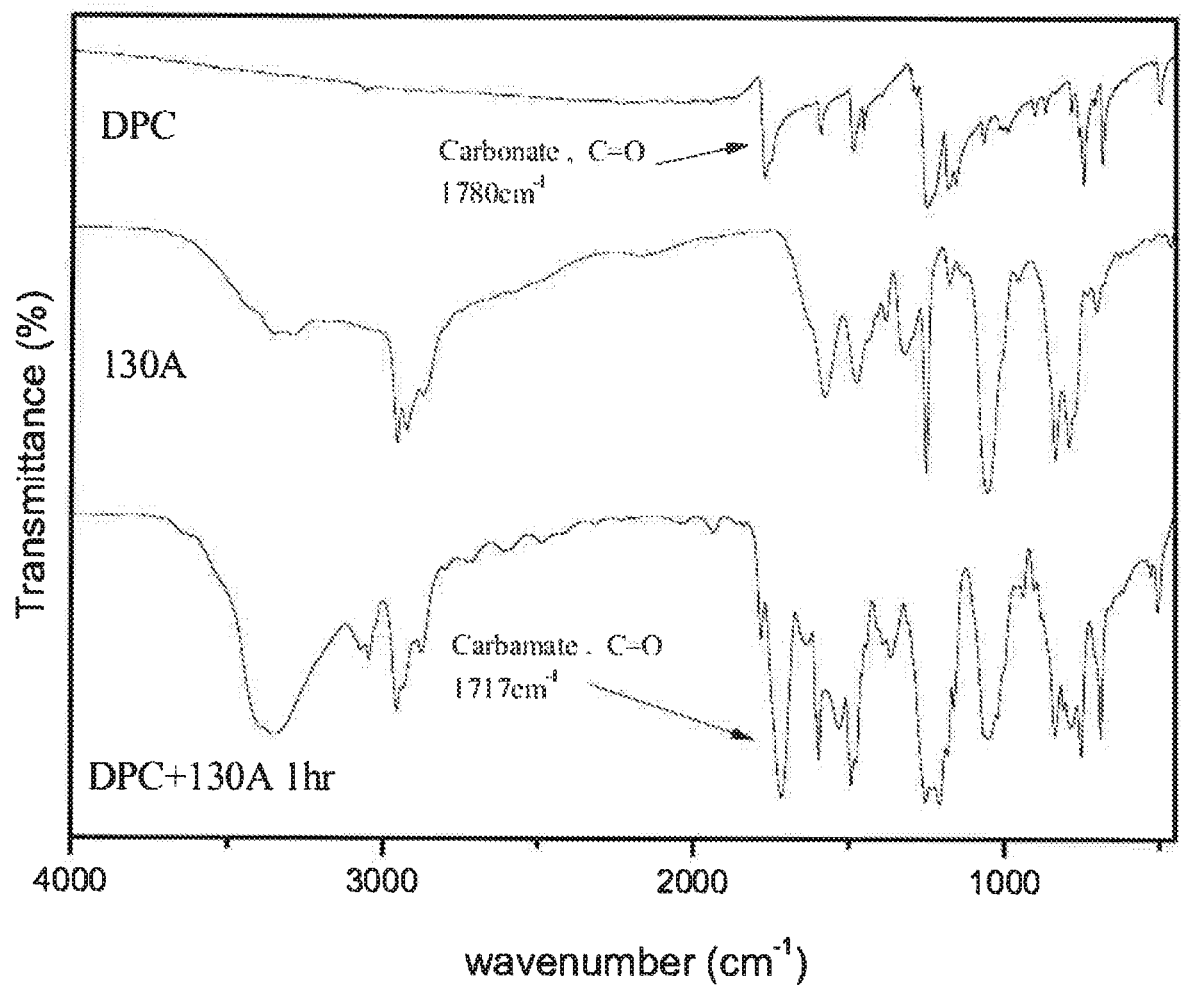
FIGS. 1a to 1c are FT-IR spectra for monitoring the synthesis of 130C, 430C, and 800C.

The concepts of the present invention are further illustrated by way of examples, which, however, are not intended to limit the scope of the present invention, and are provided for the purpose of making the disclosure of the present invention more readily apparent to those skilled in the art to which the present invention pertains.

Reagents

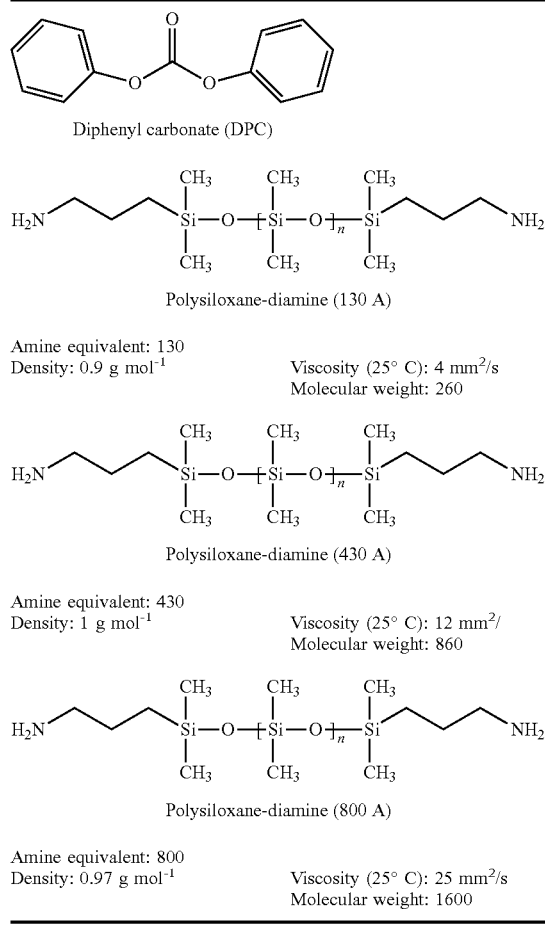

Diphenyl carbonate (DPC)

Polysiloxane-diamine (130 A)

Amine equivalent: 130
Density: 0.9 g mol$^{-1}$
Viscosity (25° C): 4 mm$^2$/s
Molecular weight: 260

Polysiloxane-diamine (430 A)

Amine equivalent: 430
Density: 1 g mol$^{-1}$
Viscosity (25° C): 12 mm$^2$/
Molecular weight: 860

Polysiloxane-diamine (800 A)

Amine equivalent: 800
Density: 0.97 g mol$^{-1}$
Viscosity (25° C): 25 mm$^2$/s
Molecular weight: 1600

1,6-Hexamethylene diisocyanate (HDI)
4,4-Methylenediphenyl diisocyanate (MDI)
Isophorone diisocyanate (IPDI)
Dicyclohexyl methane diisocyanate (H$_{12}$MDI)
m-Tetramethylxylene diisocyanate (TMXDI)
Toluene
Di-n-butyl amine
Isopropanol (IPA)
Butanediol (BDO)
Bromo cresyl blue (BPB)
Stannous octoate (T9)
Instruments and Methodologies
Fourier Transform-Infrared Spectroscopy (FT-IR)
Fourier Transform Infrared Spectrometer, Model: Perkin Elmer Spectrum One FT-IR Spectrometer
Nuclear Magnetic Resonance Spectroscopy (NMR)
Nuclear Magnetic Resonance Spectrometer, Model: Varian Unity Inova FT-NMR Spectrometer (400 Hz)
Gel Permeation Chromatography (GPC)
Chromatographic column: MBLMW-3078 (Viscotek™ ViscoGEL™ Column)
Standard: Polystyrene, M$_p$=683-1,670,000 g/mol
Mobile phase: NMP-CHROMASOLV® Plus, HPLC grade, ≥99%
Test conditions: flow rate of 1 mL/min, at a constant temperature of 40° C.
Eluting solvent: NMP
Determination of Contact Angle
Horizontally orientated contact angle meter
Model: FTA1000B
Test conditions: The samples are cut to a size of 2 cm in both length and width and placed on an instrument platform, and about 5 μL of liquid drips down to form a droplet on the sample at room temperature. Five measurements of each sample were made.
Differential Scanning Calorimetry (DSC)
Differential Scanning Calorimeter, Model: Seiko S II model SSC/6200
Test conditions: heating rate of 10° C./min and cooling rate of 50° C./min, under a nitrogen atmosphere.
Dynamic Mechanical Analysis (DMA)
Dynamic Mechanical Analyzer, Model: Perkin-Elmer Pyris Diamond
Test conditions: heating rate of 3° C./min, frequency: 1 Hz, test method: tension, and amplitude: 25 μm.
Tensile Test
Tensile tester, Model: Shimadzu EZ-SX
Test conditions: The test sample has a size as specified for an ASTM D638 standard dumbbell-shaped test specimen, and is tested at a stretch speed of 100 mm/min at room temperature. Tensile strength (MPa) and elongation (%) are calculated.

EXAMPLES

Example 1: Synthesis of a Biscarbamate Having a Siloxanyl Group in its Backbone

A 150 ml round-bottom three-neck reactor was used, into a neck of which was inserted a thermometer, and nitrogen was introduced therethrough. Another neck was fitted with a condensation tube into which cold water was introduced for condensation. A third neck was plugged with a glass stopper so that it could be opened at times for sampling to monitor the reaction by IR. 84.45 g (0.394 mol) of diphenyl carbonate (DPC) was added to the reactor and heated to 80° C. until it melted and became a liquid. 50 g (0.192 mol) of 130 A diamine was dropwise and slowly introduced via a feed tube, and the mixture was mixed by vigorous magnetic stirring in the absence of a solvent, and reacted for 1 hr. at a temperature controlled at 80° C., during which the decrease of intensity of a carbonate absorption peak at 1780 cm$^{-1}$ in the reactant and the increase of, and eventually constant, intensity of a polyurethane absorption peak at 1717 cm$^{-1}$ were indicated to monitor the reaction by IR spectroscopy. When the intensity of these peaks in the IR spectrum remained unchanged, the reaction was regarded as complete. Upon completion of the reaction, the structure was identified by NMR, and the product was a light-yellow liquid. The crude product was directly used in the preparation of a polyisocyanate. Biscarbamates having a siloxanyl group in their backbone were prepared following the same process by using various polysiloxane-diamines as raw material. The formulation is shown in Table 1.

TABLE 1

| Biscarbamate prepared | Polysiloxane-diamine | DPC |
|---|---|---|
| 130 C. | 130 A<br>50 g (0.192 mol) | 84.45 g (0.394 mol) |
| 430 C. | 430 A<br>50 g (0.058 mol) | 25.53 g (0.119 mol) |
| 800 C. | 800 A<br>50 g (0.031 mol) | 13.72 g (0.064 mol) |

Figure 1B:
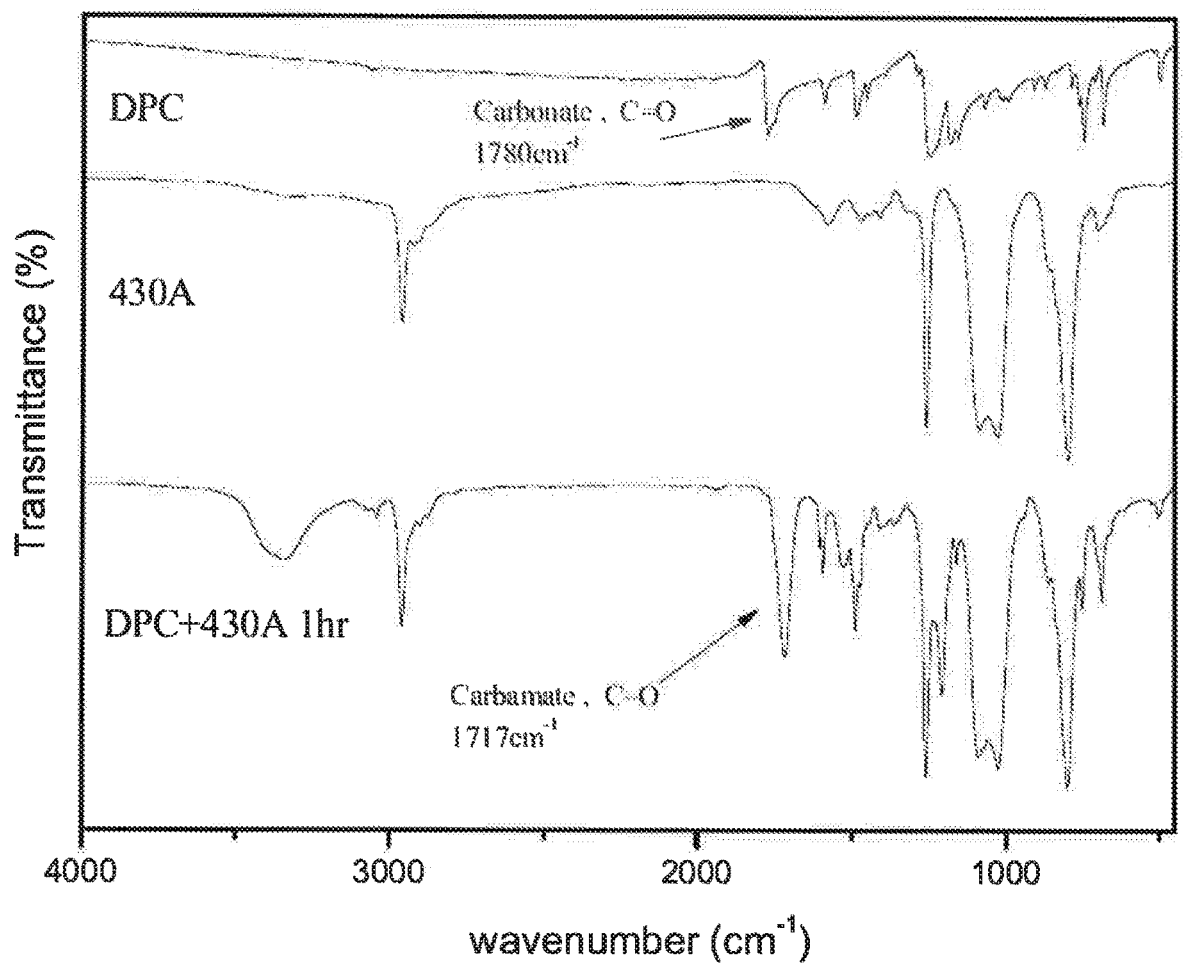
Figure 1C:
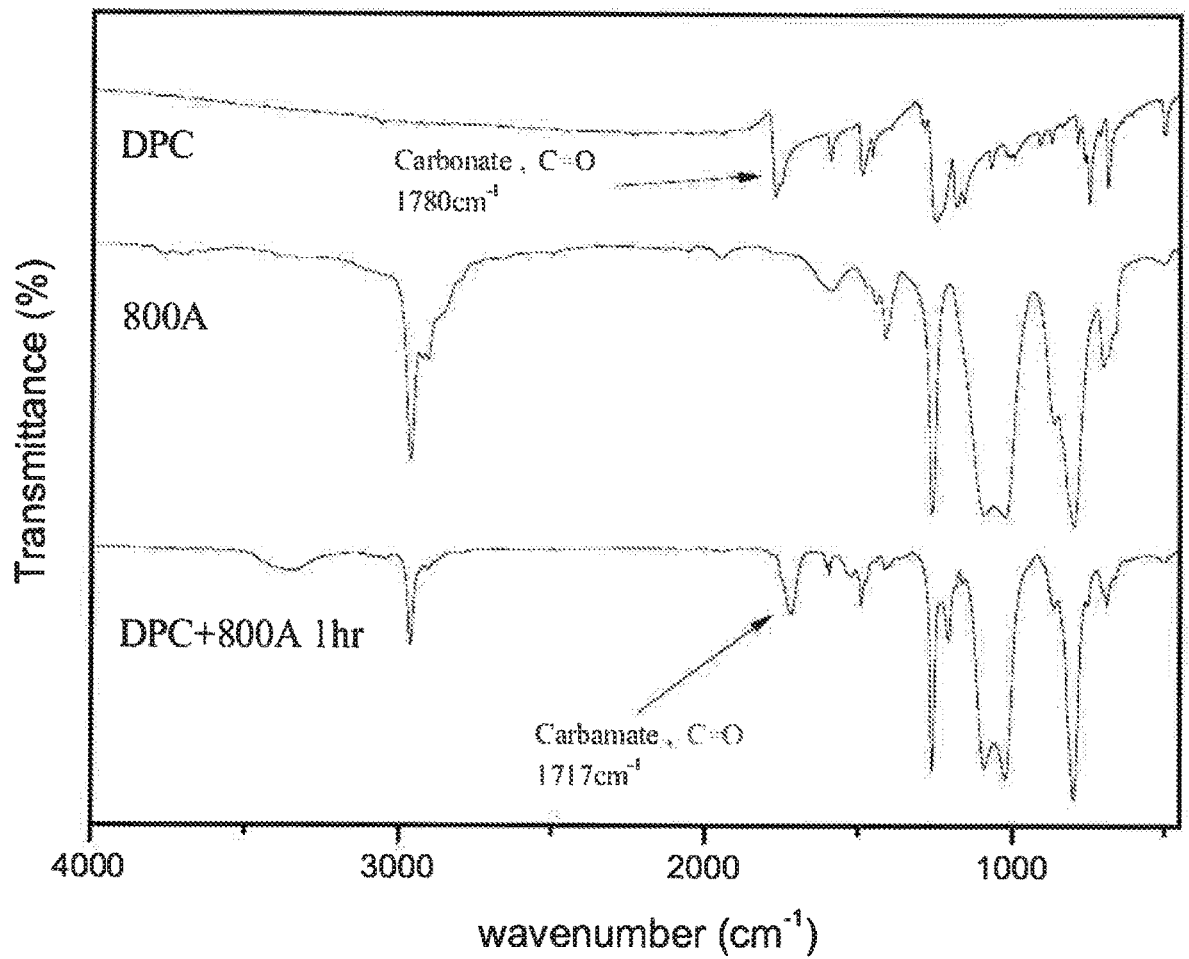

As shown in FIGS. 1a to 1c, it can be seen that the absorption peak of the C=O functional group (at 1780 cm$^{-1}$) in the reactant diphenyl carbonate disappears, and the absorption peak of the C=O functional group (at 1717 cm$^{-1}$) in the carbamate appears. After about 1 hr. after initiating the reaction, the IR spectrum does not change over time, indicating completion of the reaction. The reaction products are all in a liquid state at normal temperature. All of the hydrogen absorption peaks can be identified by $^1$H-NMR analysis, and the integral areas thereof meet with the identification of the structure.

Example 2: Synthesis of a Diisocyanate Having a Siloxanyl Group in its Backbone

The condensation tube in the apparatus used in the synthetic experiment in Example 1 was removed from the reactor, and replaced with a combined distillation tube (fitted with a thermometer). At one end of the tube, a one-neck flask was connected for receiving the by-product phenol produced during cracking. Then, a vacuum pump was connected, such that the cracking reaction was carried out with rapid stirring at a reduced pressure (7 cmHg). The reaction temperature was raised to 170° C. for 2 hrs., and the 130C/430C/800C biscarbamates synthesized above were cracked into products mainly characterized by isocyanate functional groups, which were 130I/430I/800I respectively. During the reaction process, the by-product phenol produced via decomposition was collected at the same time, and the cracking reaction was monitored by IR spectroscopy, until the absorption peak of the biscarbamate (at 1717 cm$^{-1}$) disappeared, and the intensity of the absorption peaks of the isocyanate (at 2270 cm$^{-1}$) and other co-products (for example, a trimer (at 1701 cm$^{-1}$) and an allophanate (at 1730 cm$^{-1}$)) remained unchanged. The resulting products, without further purification, were directly used in the content determination by the titration of isocyanates, and in the preparation of PU.

NCO % of the isocyanates prepared is shown in Table 2 below.

TABLE 2

|      | Equivalent | NCO % |
|------|------------|-------|
| 130I | 645        | 6.5%  |
| 430I | 700        | 6%    |
| 800I | 1220       | 3.5%  |

Figure 2A:
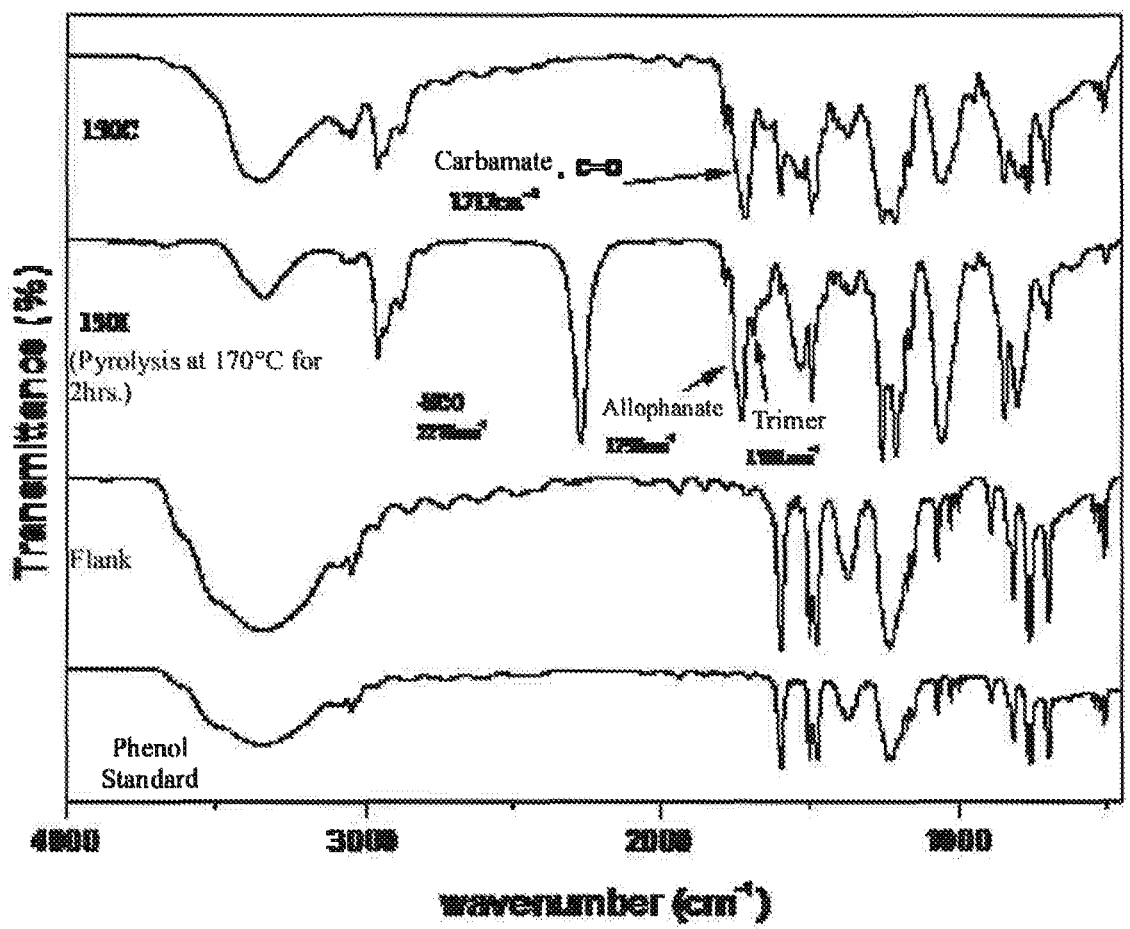
FIGS. 2a to 2c are FT-IR spectra for monitoring the synthesis of 130I, 430I, and 800I.
Figure 2B:
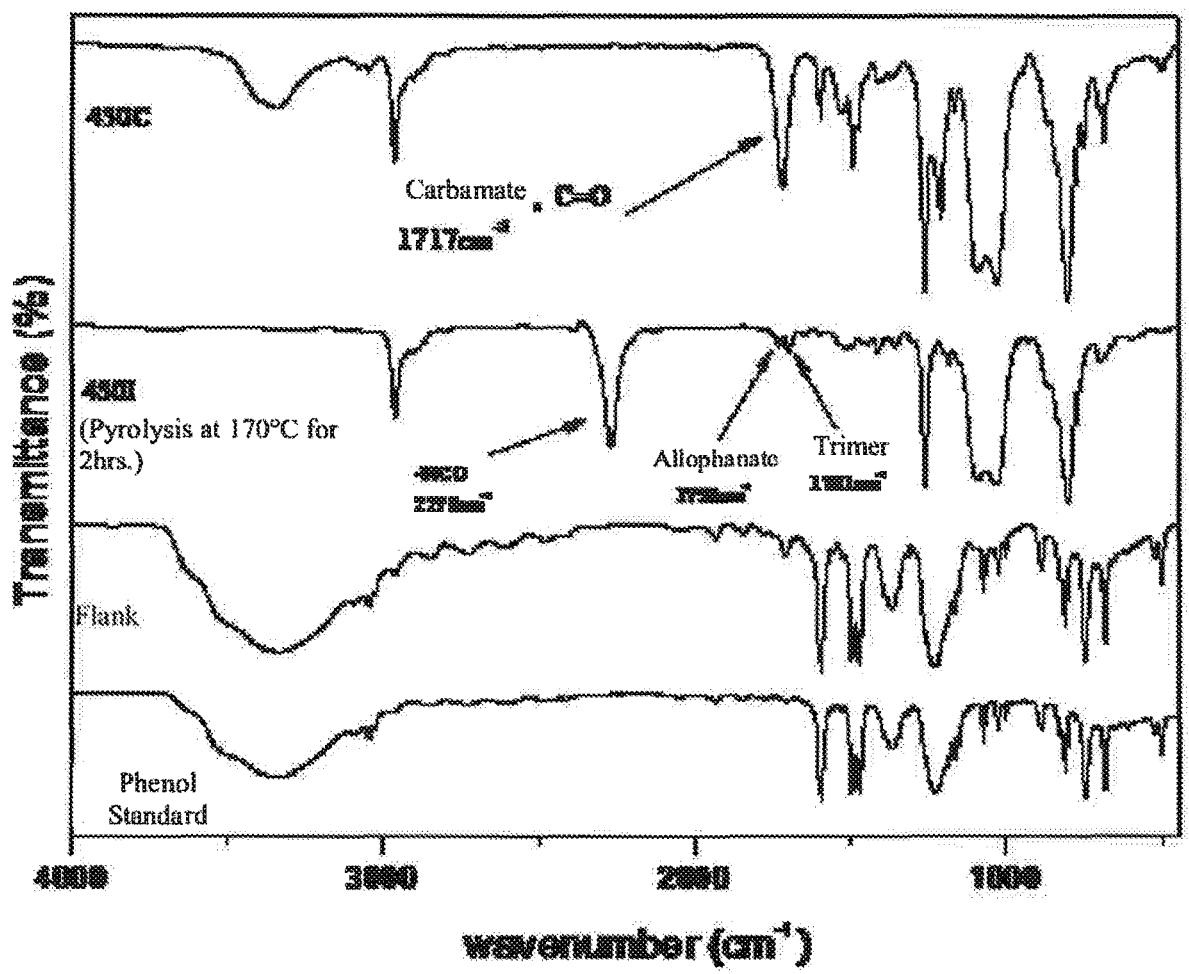
Figure 2C:
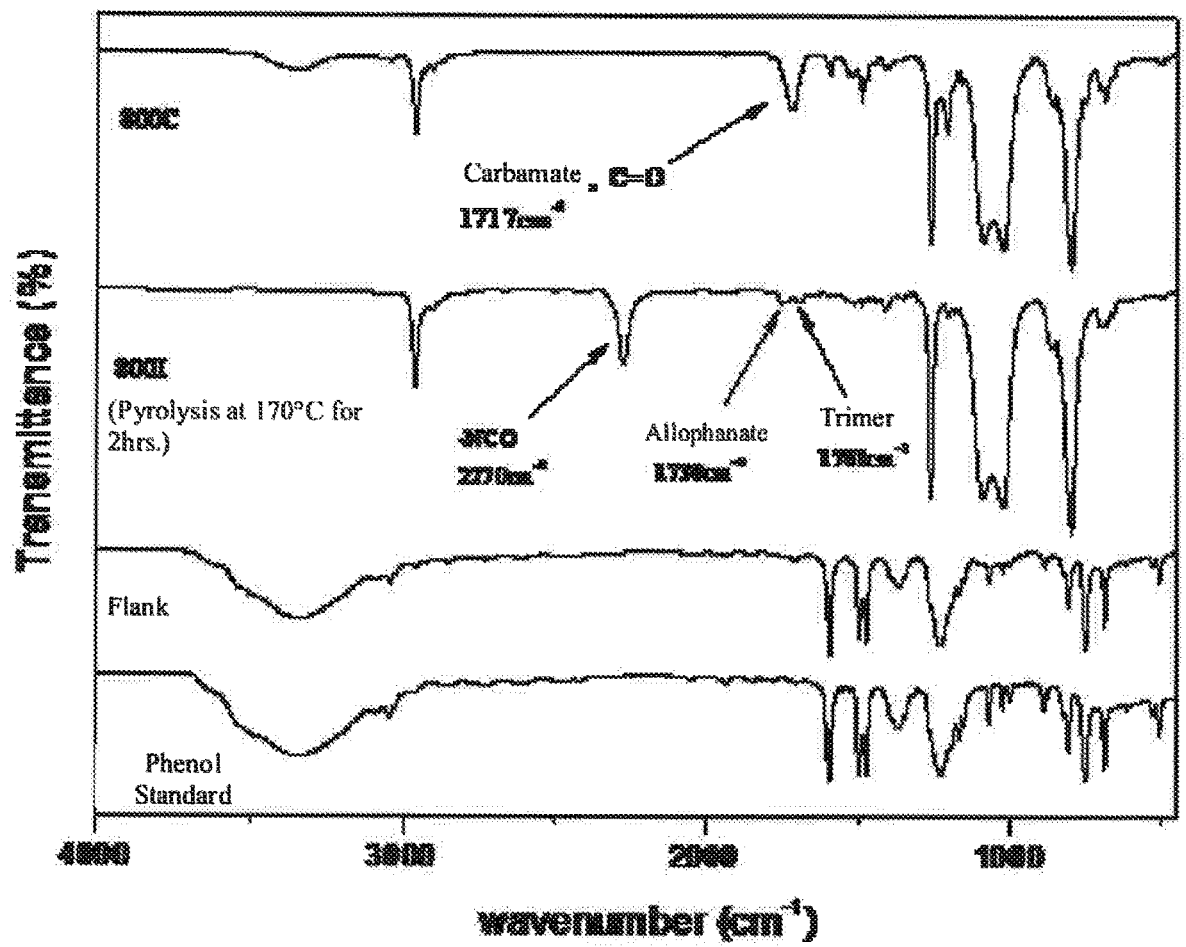

As shown in FIGS. 2a to 2c, it can be found that during the cracking process, the absorption peak of the carbamate (at 1717 cm$^{-1}$) disappears, and the absorption peaks of the isocyanate (NCO) (at 2273 cm$^{-1}$) and a small amount of other co-products (for example, a trimer (at 1701 cm$^{-1}$) and an allophanate (at 1730 cm$^{-1}$)) appear. In addition, the IR spectrum of the phenol thus collected is consistent with that of the standard, and 92 to 97% of phenol is recovered. It is suggested that the reaction is complete, the yield is extremely high, and the recovery rate of the by-product phenol is also good. The prepared isocyanate, without further processing or refining, was directly used in the synthesis of a polyurethane (PU).

During the synthesis of the isocyanate having a soft segment in the present invention, no undesired by-product urea was detected, and the reaction can take place without needing to add any solvent or catalyst, which meets the demand for green chemical synthesis of isocyanates. Moreover, in the green chemical synthesis of isocyanates, the synthesis efficiency is not impacted, the yield of the product is extremely high, and the recovery rate of the by-product phenol can be up to 90%, or even 97% or above.

Example 3: Synthesis of a Polyurethane Having a Siloxanyl Group in its Backbone (Isocyanate: 130I; and Chain Extender: IPDI)

A disconnecting-type 150 ml four-neck round-bottom flask was used; a right central neck of which was fitted with a mechanically stirred reactor, into another neck of the reactor was inserted a thermometer and nitrogen was introduced therethrough. Yet another neck was fitted with a condensation tube into which cold water was introduced. A fourth neck was plugged with a glass stopper, so that a small amount of sample could be taken out for monitoring the progress of reaction if needed. 23 g of toluene was added as a solvent to the round-bottom flask, then 1.35 g of excessive butanediol (BDO) and 6.45 g of 130I were added, and a drop of T9 was added, and the mixture was reacted at 80° C. for 1 hr. The reaction of 130-I with BDO to form a prepolymer having a soft segment and containing a terminal hydroxyl group was determined to be complete by FT-IR. Subsequently, 2.22 g of IPDI was added and reacted for 2 hrs. at 80° C. with stirring for chain extension. Then, the solution was poured into an aluminum dish and placed for 24 hrs. in an oven at 60° C., and toluene was removed by volatilization to form a PU film, which was designated as 130BI-30.

The contents of BDO, IPDI, and the solvent toluene were adjusted, and 130BI-40 and 130BI-50 having a different proportion of hard segments were prepared following the same synthesis process. The details are given in Table 3-1.

TABLE 3-1

| | Raw material | | | | |
|---|---|---|---|---|---|
| Product | 130I (g) | BDO (g) | IPDI (g) | Toluene (S.C = 30%) | BDO + IPDI, wt. % (calculated) |
| 130BI-30 | 6.45 | 1.35 | 2.22 | 23 | 36 |
| Equivalent ratio | 1 | 3 | 2 | | |
| 130BI-40 | 6.45 | 1.8 | 3.34 | 27 | 44 |
| Equivalent ratio | 1 | 4 | 3 | | |
| 130BI-50 | 6.45 | 2.7 | 5.56 | 34 | 56 |
| Equivalent ratio | 1 | 6 | 5 | | |

The properties of the prepared PU films (130BI-30, 130BI-40, and 130BI-50) comprising a different proportion by weight of hard segments were respectively tested. The results are shown in Table 3-2.

TABLE 3-2

| | | | | Contact | $T_g$ (° C.) | | Tensile strength | Elongation |
|---|---|---|---|---|---|---|---|---|
| | Mn | Mw | PD | angle | DSC | DMA | (Mpa) | (%) |
| 130BI-30 | 52200 | 75800 | 1.45 | 90° | −7 | 50 | 4.9 | 285 |
| 130BI-40 | 9800 | 20000 | 4.8 | 88° | 6 | 66 | 11 | 200 |

TABLE 3-2-continued

|  | Mn | Mw | PD | Contact angle | $T_g$ (° C.) DSC | $T_g$ (° C.) DMA | Tensile strength (Mpa) | Elongation (%) |
|---|---|---|---|---|---|---|---|---|
| 130BI-50 | 8000 | 14000 | 1.73 | 86° | 12 | 81 | 13.6 | 153 |

Example 4: Synthesis of a Polyurethane Having a Siloxanyl Group in its Backbone (Isocyanate: 430I; and Chain Extender: IPDI)

Following the same synthesis method as that in Example 3, 430BI-30, 430BI-40, and 430BI-50 having a different proportion of hard segments were prepared with 430I as a reactant, where the amounts of the reagents and the solvent are shown in Table 4-1.

TABLE 4-1

| Product | Raw material 430I (g) | BDO (g) | IPDI (g) | Toluene S.C = 30% | BDO + IPDI wt. % (calculated) |
|---|---|---|---|---|---|
| 430BI-30 | 7 | 1.35 | 2.22 | 25 | 34 |
| Equivalent ratio | 1 | 3 | 2 | | |
| 430BI-40 | 7 | 1.8 | 3.33 | 28 | 42 |
| Equivalent ratio | 1 | 4 | 3 | | |
| 430BI-50 | 7 | 2.7 | 5.56 | 35 | 54 |
| Equivalent ratio | 1 | 6 | 5 | | |

The properties of the prepared PU films (430BI-30, 430BI-40, and 430BI-50) comprising a different proportion by weight of hard segments were respectively tested. The results are shown in Table 4-2.

TABLE 4-2

|  | Mn | Mw | PD | Contact angle | $T_g$ (° C.) DSC | $T_g$ (° C.) DMA | Tensile strength (Mpa) | Elongation (%) |
|---|---|---|---|---|---|---|---|---|
| 430BI-30 | 23700 | 35400 | 1.5 | 96° | −20 | 35 | 2.1 | 290 |
| 430BI-40 | 9300 | 16200 | 1.74 | 98° | 5 | 55 | 2.7 | 260 |
| 430BI-50 | 11300 | 20000 | 1.74 | 100° | 25 | 72 | 6.8 | 90 |

Example 5: Synthesis of a Polyurethane Having a Siloxanyl Group in its Backbone (Isocyanate: 800I; and Chain Extender: IPDI)

Following the same synthesis method as that in Example 3, 800BI-30, 800BI-40, and 800BI-50 having a different proportion of hard segments were prepared with 800I as a reactant, where the amounts of the reagents and the solvent are shown in Table 5-1.

TABLE 5-1

| Product | Raw material 800I (g) | BDO (g) | IPDI (g) | Toluene (S.C = 30%) | BDO + IPDI wt. % (calculated) |
|---|---|---|---|---|---|
| 800BI-30 | 6.1 | 0.9 | 1.67 | 20 | 30 |
| Equivalent ratio | 1 | 4 | 3 | | |
| 800BI-40 | 6.1 | 1.35 | 2.78 | 24 | 40 |
| Equivalent ratio | 1 | 6 | 5 | | |
| 800BI-50 | 6.1 | 2.03 | 4.45 | 30 | 52 |
| Equivalent ratio | 1 | 9 | 8 | | |

The properties of the prepared PU films (800BI-30, 800BI-40, and 800BI-50) comprising a different proportion by weight of hard segments were respectively tested. The results are shown in Table 5-2.

TABLE 5-2

|  | Mn | Mw | PD | Contact angle | $T_g$ (° C.) DSC | $T_g$ (° C.) DMA | Tensile strength (Mpa) | Elongation (%) |
|---|---|---|---|---|---|---|---|---|
| 800BI-30 | 114500 | 142800 | 1.24 | 92° | −55 | 52 | 5.1 | 350 |
| 800BI-40 | 113800 | 153900 | 1.35 | 93° | −50 | 79 | 6.2 | 310 |
| 800BI-50 | 100500 | 187600 | 1.86 | 97° | −43 | 98 | 10.6 | 200 |

Example 6: Synthesis of a Polyurethane Having a Siloxanyl Group in its Backbone (Isocyanate: 130I; and Chain Extender: TMXDI)

A disconnecting-type 150 ml four-neck round-bottom flask was used; a right central neck of which was fitted with a mechanically stirred reactor, into another neck of the reactor was inserted a thermometer and nitrogen was introduced therethrough. Yet another neck was fitted with a condensation tube into which cold water was introduced. A fourth neck was plugged with a glass stopper, so that a small amount of sample could be taken out for monitoring the progress of reaction if needed. 24 g of toluene was added as a solvent to the round-bottom flask, then 1.35 g of excessive butanediol (BDO) and 6.45 g of 130I were added, and a drop of T9 was added, and the mixture was reacted at 80° C. for 1 hr. The reaction of 130-I with BDO to form a prepolymer having a soft segment was determined to be complete by FT-IR. Subsequently, 2.44 g of TMXDI was added and reacted for 2 hrs. at 100° C. with stirring, for chain extension. Then, the solution was poured into an aluminum dish and placed for 24 hrs. in an oven at 60° C., and toluene was removed by volatilization to form a PU film, which was designated as 130BT-30.

The contents of BDO, TMXDI and the solvent toluene were adjusted, and 130BT-40 and 130BT-50 having a different proportion of hard segments were prepared following the same synthesis process. The details are given in Table 6-1.

TABLE 6-1

| | Raw material | | | | |
|---|---|---|---|---|---|
| Product | 130I (g) | BDO (g) | TMXDI (g) | Toluene (S.C = 30%) | BDO + TMXDI wt. % (calculated) |
| 130BT-30 | 6.45 | 1.35 | 2.44 | 24 | 37 |
| Equivalent ratio | 1 | 3 | 2 | | |
| 130BT-40 | 6.45 | 1.8 | 3.66 | 28 | 46 |
| Equivalent ratio | 1 | 4 | 3 | | |
| 130BT-50 | 6.45 | 2.7 | 6.11 | 36 | 58 |
| Equivalent ratio | 1 | 6 | 5 | | |

The properties of the prepared PU films (130BT-30, 130BT-40, and 130BT-50) comprising a different proportion by weight of hard segments were respectively tested. The results are shown in Table 6-2.

TABLE 6-2

| | | | | Contact | $T_g$ (° C.) | | Tensile strength | Elongation |
|---|---|---|---|---|---|---|---|---|
| | Mn | Mw | PD | angle | DSC | DMA | (Mpa) | (%) |
| 130BT-30 | 3500 | 8400 | 2.4 | 99° | 5 | 47 | 0.8 | 665 |
| 130BT-40 | 40700 | 61300 | 1.5 | 106° | 10 | 54 | 3.8 | 440 |
| 130BT-50 | 42200 | 66200 | 1.6 | 90° | 15 | 53 | 6.4 | 455 |

Example 7: Synthesis of a Polyurethane Having a Siloxanyl Group in its Backbone (Isocyanate: 430I; and Chain Extender: TMXDI)

Following the same synthesis method as that in Example 6, 430BT-30, 430BT-40, and 430BT-50 having a different proportion of hard segments were prepared with 430I as a reactant and TMXDI as a chain extender, where the amounts of the reagents and the solvent are shown in Table 7-1.

TABLE 7-1

| | Raw material | | | | |
|---|---|---|---|---|---|
| Product | 430I (g) | BDO (g) | TMXDI (g) | Toluene (S.C = 30%) | BDO + TMXDI wt. % (calculated) |
| 430BT-30 | 7 | 1.35 | 2.44 | 25 | 35 |
| Equivalent ratio | 1 | 3 | 2 | | |
| 430BT-40 | 7 | 1.8 | 3.66 | 29 | 44 |
| Equivalent ratio | 1 | 4 | 3 | | |
| 430BT-50 | 7 | 2.7 | 6.11 | 37 | 56 |
| Equivalent ratio | 1 | 6 | 5 | | |

The properties of the prepared PU films (430BT-30, 430BT-40, and 430BT-50) comprising a different proportion by weight of hard segments were respectively tested. The results are shown in Table 7-2.

TABLE 7-2

|  | Mn | Mw | PD | Contact angle | $T_g$ (° C.) DSC | $T_g$ (° C.) DMA | Tensile strength (Mpa) | Elongation (%) |
|---|---|---|---|---|---|---|---|---|
| 430BT-30 | 9800 | 20700 | 2.1 | 112° | −10 | 26 | 1.5 | 1100 |
| 430BT-40 | 38800 | 55000 | 1.4 | 98° | 0 | 38 | 2 | 1200 |
| 430BT-50 | 36300 | 45400 | 1.3 | 95° | 12 | 57 | 9 | 590 |

Example 8: Synthesis of a Polyurethane Having a Siloxanyl Group in its Backbone (Isocyanate: 800I; and Chain Extender: TMXDI)

Following the same synthesis method as that in Example 6, 800BT-30, 800BT-40, and 800BT-50 having a different proportion of hard segments were prepared with 800I as a reactant and TMXDI as a chain extender, where the amounts of the reagents and the solvent are shown in Table 8-1.

TABLE 8-1

| | Raw material | | | | |
|---|---|---|---|---|---|
| Product | 800I (g) | BDO (g) | TMXDI (g) | Toluene (S.C = 30%) | BDO + TMXDI wt. % (calculated) |
| 800BT-30 | 6.1 | 0.9 | 1.83 | 21 | 31 |
| Equivalent ratio | 1 | 4 | 3 | | |
| 800BT-40 | 6.1 | 1.35 | 3.05 | 25 | 42 |
| Equivalent ratio | 1 | 6 | 5 | | |
| 800BT-50 | 6.1 | 2.03 | 4.89 | 30 | 53 |
| Equivalent ratio | 1 | 9 | 8 | | |

The properties of the prepared PU films (800BT-30, 800BT-40, and 800BT-50) comprising a different proportion by weight of hard segments were respectively tested. The results are shown in Table 8-2.

TABLE 8-2

|  | Mn | Mw | PD | Contact angle | $T_g$ (° C.) DSC | $T_g$ (° C.) DMA | Tensile strength (Mpa) | Elongation (%) |
|---|---|---|---|---|---|---|---|---|
| 800BT-30 | 8400 | 13500 | 1.6 | 105° | −40 | 38 | 2.6 | 730 |
| 800BT-40 | 8300 | 12800 | 1.6 | 113° | −30 | 55 | 3.2 | 500 |
| 800BT-50 | 10300 | 18600 | 1.8 | 93° | −20 | 65 | 7.6 | 253 |

Example 9: Synthesis of a Polyurethane Having a Siloxanyl Group in its Backbone (Isocyanate: 130I; and Chain Extender: $H_{12}$MDI)

A disconnecting-type 150 ml four-neck round-bottom flask was used; a right central neck of which was fitted with a mechanically stirred reactor, into another neck of the reactor was inserted a thermometer and nitrogen was introduced therethrough. Yet another neck was fitted with a condensation tube into which cold water was introduced. A fourth neck was plugged with a glass stopper, so that a small amount of sample could be taken out for monitoring the progress of reaction if needed. 24 g of toluene was added as a solvent to the round-bottom flask, then 1.35 g of excessive butanediol (BDO) and 6.45 g of 130I were added, and a drop of T9 was added, and the mixture was reacted at 80° C. for 1 hr. The reaction of 130-I with BDO to form a prepolymer having a soft segment was determined to be complete by FT-IR. Subsequently, 2.62 g of $H_{12}$MDI was added and reacted for 1 hr. at 100° C. with stirring, for chain extension. Then, the solution was poured into an aluminum dish and placed for 24 hrs. in an oven at 60° C., and toluene was removed by volatilization to form a PU film, which was designated as 130BH$_{12}$-30.

The contents of BDO, $H_{12}$MDI and the solvent toluene were adjusted, and 130BT-40 and 130BT-50 having a different proportion of hard segments were prepared following the same synthesis process. The details are given in Table 9-1.

TABLE 9-1

| | Raw material | | | | |
|---|---|---|---|---|---|
| Product | 130I (g) | BDO (g) | $H_{12}$MDI (g) | Toluene (S.C = 30%) | BDO + $H_{12}$MDI wt. % (calculated) |
| 130BH$_{12}$-30 | 6.45 | 1.35 | 2.62 | 24 | 38 |
| Equivalent ratio | 1 | 3 | 2 | | |
| 130BH$_{12}$-40 | 6.45 | 1.8 | 3.94 | 28 | 47 |
| Equivalent ratio | 1 | 4 | 3 | | |
| 130BH$_{12}$-50 | 6.45 | 2.7 | 6.56 | 37 | 59 |
| Equivalent ratio | 1 | 6 | 5 | | |

The properties of the prepared PU films (130BH$_{12}$-30, 130BH$_{12}$-40, and 130BH$_{12}$-50) comprising a different proportion by weight of hard segments were respectively tested. The results are shown in Table 9-2.

TABLE 9-2

| | Mn | Mw | PD | Contact angle | T$_g$ (° C.) DSC | T$_g$ (° C.) DMA | Tensile strength (Mpa) | Elongation (%) |
|---|---|---|---|---|---|---|---|---|
| 130BH$_{12}$-30 | 48300 | 89800 | 1.9 | 108° | −3 | 48 | 4.4 | 254 |
| 130BH$_{12}$-40 | 45600 | 86200 | 1.9 | 110° | 5 | 52 | 10 | 163 |
| 130BH$_{12}$-50 | 35000 | 49300 | 1.8 | 112° | 10 | — | — | — |

Example 10: Synthesis of a Polyurethane Having a Siloxanyl Group in its Backbone (Isocyanate: 430I; and Chain Extender: H$_{12}$MDI)

Following the same synthesis method as that in Example 9, 430BH$_{12}$-30, 430BH$_{12}$-40, and 430BH$_{12}$-50 having a different proportion of hard segments were prepared with 430I as a reactant and H$_{12}$MDI as a chain extender, where the amounts of the reagents and the solvent are shown in Table 10-1.

TABLE 10-1

| | Raw material | | | | |
|---|---|---|---|---|---|
| Product | 430I (g) | BDO (g) | H$_{12}$MDI (g) | Toluene (S.C = 30%) | BDO + H$_{12}$MDI wt. % (calculated) |
| 430BH$_{12}$-30 | 7 | 1.35 | 2.62 | 26 | 36 |
| Equivalent ratio | 1 | 3 | 2 | | |
| 430BH$_{12}$-40 | 7 | 1.8 | 3.94 | 30 | 45 |
| Equivalent ratio | 1 | 4 | 3 | | |
| 430BH$_{12}$-50 | 7 | 2.7 | 6.56 | 38 | 57 |
| Equivalent ratio | 1 | 6 | 5 | | |

The properties of the prepared PU films (430BH$_{12}$-30, 430BH$_{12}$-40, and 430BH$_{12}$-50) comprising a different proportion by weight of hard segments were respectively tested. The results are shown in Table 10-2.

TABLE 10-2

| | Mn | Mw | PD | Contact angle | T$_g$ (° C.) DSC | T$_g$ (° C.) DMA | Tensile strength (Mpa) | Elongation (%) |
|---|---|---|---|---|---|---|---|---|
| 430BH$_{12}$-30 | 9600 | 16300 | 1.7 | 106° | −15 | −28 | 4.2 | 97 |
| 430BH$_{12}$-40 | 43300 | 67400 | 1.6 | 110° | −10 | 82 | 10.6 | 89 |
| 430BH$_{12}$-50 | 27800 | 41300 | 1.5 | 108° | −5 | 108 | 14.8 | 38 |

Example 11: Synthesis of a Polyurethane Having a Siloxanyl Group in its Backbone (Isocyanate: 800I; and Chain Extender: H$_{12}$MDI)

Following the same synthesis method as that in Example 9, 800BH$_{12}$-30, 800BH$_{12}$-40, and 800BH$_{12}$-50 having a different proportion of hard segments were prepared with 800I as a reactant and H$_{12}$MDI as a chain extender, where the amounts of the reagents and the solvent are shown in Table 11-1.

TABLE 11-1

| | Raw material | | | | |
|---|---|---|---|---|---|
| Product | 800I (g) | BDO (g) | H$_{12}$MDI (g) | Toluene (S.C = 30%) | BDO + H$_{12}$MDI wt. % (calculated) |
| 800BH$_{12}$-30 | 6.1 | 0.9 | 1.97 | 21 | 32 |
| Equivalent ratio | 1 | 3 | 2 | | |
| 800BH$_{12}$-40 | 6.1 | 1.35 | 3.28 | 25 | 43 |
| Equivalent ratio | 1 | 4 | 3 | | |
| 800BH$_{12}$-50 | 6.1 | 2.03 | 5.25 | 31 | 54 |
| Equivalent ratio | 1 | 6 | 5 | | |

The properties of the prepared PU films (800BH$_{12}$-30, 800BH$_{12}$-40, and 800BH$_{12}$-50) comprising a different proportion by weight of hard segments were respectively tested. The results are shown in Table 11-2.

TABLE 11-2

| | Mn | Mw | PD | Contact angle | $T_g$ (° C.) DSC | $T_g$ (° C.) DMA | Tensile strength (Mpa) | Elongation (%) |
|---|---|---|---|---|---|---|---|---|
| 800BH$_{12}$-30 | 54600 | 91200 | 1.7 | 107° | −55 | −43 | — | 1.8 | 60 |
| 800BH$_{12}$-40 | 101300 | 151200 | 1.5 | 110° | −46 | −38 | 110 | 7.3 | 89 |
| 800BH$_{12}$-50 | 87200 | 122100 | 1.4 | 112° | −30 | −33 | 105 | 8.3 | 58 |

Therefore, the polyisocyanate having a soft segment synthesized by a non-phosgene method provided in the present invention can be used as a raw material in the synthesis of polyurethanes having a soft segment, and can be used in combination with various polyols and chain extenders to synthesize polyurethanes which meet the practical requirements. For example, the mechanical properties can be strengthened by increasing the molecular weight. Better elongation or phase separation can also be achieved by the use of different chain extenders.

The polyurethane synthesized in the present invention has properties such as low degree of dyeing, high transparency, high thermal stability, smooth tactile feel and hydrophobicity compared with conventional polyurethanes. Particularly, the polyurethane synthesized in the present invention has a tensile strength of up to 15 Mpa, which is comparable to that (>10 Mpa) exhibited by conventional polyurethanes. In addition, all the polyurethanes exhibit a glass transition temperature over a wide range, and a variety of polyurethanes exhibit a phase change, thus having tolerability to temperatures over a wide range. The present polyurethane has an elongation up to 1200%, which meets the physical property requirement for common polyurethane products, and can be applied in areas requiring high softness, such as in fabric treatment or in disposable gloves, and the working temperature range is wider than traditional polyurethane products. On the other hand, because of the presence of a hydrophobic soft segment, the synthesized polyurethane exhibits a contact angle (at least 90°, for example >1000, and up to 110 to 115° or higher) required for hydrophobicity, and thus can be further applied to products requiring hydrophobic properties.

It will be apparent to those skilled in the art that various changes and modifications may be made to the structure of the present invention without departing from the scope or spirit of the invention. In view of the above, the present invention is intended to contemplate modifications and variations of the present invention provided that such modifications and variations are within the scope of the following claims and equivalents thereof.

The above-described embodiments of the present invention are intended to be illustrative only. Numerous alternative embodiments may be devised by persons skilled in the art without departing from the scope of the following claims.

What is claimed is:

1. A non-phosgene method for synthesizing a polyisocyanate having siloxanyl group iii its backbone, comprising: thermally cracking a multi-functional carbamate having a siloxanyl group in its backbone.

2. The method according to claim 1, wherein the multi-functional carbamate having a siloxanyl group in its backbone is prepared by reacting a polyamine having a siloxanyl group with a diaryl carbonate.

3. The method according to claim 2, wherein the polyamine having a siloxanyl group is a diamine of Formula (2) below:

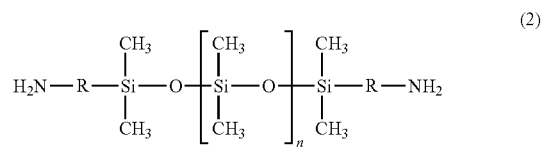

in which each R independently represents a linear or branched $C_{1-16}$ hydrocarbylene or a $C_{3-16}$ cyclohydrocarbylene, and n is from 2 to 30.

4. The method according to claim 2, wherein the diaryl carbonate is represented by Formula (3) below:

in which $R^1$ and $R^2$ independently represent an aromatic group having 6 to 30 carbon atoms.

5. The method according to claim 2, wherein the molar ratio of the diamine having a siloxanyl group to the diaryl carbonate is in the range of from 1:2 to 1:6.

6. The method according to claim 2, which is a one-pot method.

7. A method for synthesizing a polyurethane having a siloxanyl group in its backbone, comprising reacting a polyisocyanate having a siloxanyl group in its backbone, a polyol, and an optional chain extender, wherein the polyisocyanate having a siloxanyl group in its backbone is prepared by the method according to claim 1.

8. The method according to claim 7, wherein the polyisocyanate having a siloxanyl group in its backbone is reacted with the polyol to form a prepolymer before the reaction to form the polyurethane is carried out.

9. The method according to claim 7, which is a one-pot method comprising the following steps carried out in the same reactor: reacting a polyamine having a siloxanyl group with a diaryl carbonate to produce a multi-functional carbamate having a siloxanyl group in its backbone; thermally cracking the multi-functional carbamate to produce a polyisocyanate having a siloxanyl group in its backbone; and further adding a polyol and an optional chain extender and reacting under suitable reaction conditions to produce a polyurethane having a siloxanyl group in its backbone.

10. The method according to claim 7, wherein the polyurethane comprises a hard segment and wherein the percentages by weight of the hard segment are from 20 to 70%.

* * * * *